United States Patent
Hinchliffe et al.

(10) Patent No.: US 8,398,673 B2
(45) Date of Patent: Mar. 19, 2013

(54) SURGICAL INSTRUMENT FOR GRASPING AND CUTTING TISSUE

(75) Inventors: Peter W. J. Hinchliffe, Campbell Hall, NY (US); Adam I. Lehman, Northford, CT (US); Daniel Helme, Warren, NJ (US); Norbert Thomas Jankowski, Pompano Beach, FL (US); Joel N. Helfer, Cheshire, CT (US)

(73) Assignee: Surgical Innovations V.O.F., Elspat (NL)

( * ) Notice: Subject to any disclaimer, the term of this patent is extended or adjusted under 35 U.S.C. 154(b) by 740 days.

(21) Appl. No.: 12/322,729

(22) Filed: Feb. 6, 2009

(65) Prior Publication Data

US 2009/0209991 A1   Aug. 20, 2009

Related U.S. Application Data

(60) Provisional application No. 61/066,063, filed on Feb. 15, 2008.

(51) Int. Cl.
*A61B 17/00* (2006.01)
(52) U.S. Cl. ........................................... 606/205
(58) Field of Classification Search .................. 606/167, 606/170, 174, 205–208
See application file for complete search history.

(56) References Cited

U.S. PATENT DOCUMENTS

| | | | |
|---|---|---|---|
| 2,278,720 A | 4/1942 | Follet | |
| 4,576,408 A | 3/1986 | Maneki | |
| 4,655,216 A | 4/1987 | Tischer | |
| 4,944,093 A | 7/1990 | Falk | |
| 5,147,373 A | 9/1992 | Ferzli | |
| 5,171,257 A | 12/1992 | Ferzli | |
| 5,176,702 A | 1/1993 | Bales et al. | |
| 5,254,129 A | 10/1993 | Alexander | |
| 5,254,130 A | 10/1993 | Poncet et al. | |
| 5,275,615 A | 1/1994 | Rose | |
| 5,282,826 A | 2/1994 | Quadri | |
| 5,312,391 A | 5/1994 | Wilk | |
| 5,318,221 A | 6/1994 | Green et al. | |
| 5,342,381 A | 8/1994 | Tidemand | |
| 5,403,312 A | 4/1995 | Yates et al. | |
| 5,456,684 A | 10/1995 | Schmidt et al. | |
| 5,456,695 A | 10/1995 | Herve Dallemagne | |
| 5,496,317 A | 3/1996 | Goble et al. | |
| 5,573,535 A | 11/1996 | Viklund | |
| 5,613,977 A | 3/1997 | Weber et al. | |
| 5,626,595 A | 5/1997 | Sklar et al. | |
| 5,626,608 A | 5/1997 | Cuny et al. | |

(Continued)

FOREIGN PATENT DOCUMENTS

| | | |
|---|---|---|
| DE | 3322741 | 1/1985 |
| DE | 4400409 | 7/1995 |

(Continued)

*Primary Examiner* — Ryan Severson
*Assistant Examiner* — Katherine M Shi

(57) ABSTRACT

A surgical instrument for cutting and grasping tissue comprising a handle assembly, an elongated member and first and second jaws. A first movable member moves the second jaw in a first direction about a first pivot axis in a grasping action and a second movable member moves the second jaw in a second direction different than the first direction and about a second pivot axis in a cutting action. A switch is positioned at the proximal portion of the instrument and a selecting member is actuated by movement of the switch, the selecting member movable between a first position to enable movement of the second jaw in the first direction and prohibit movement in the second direction and a second position to enable movement of the second jaw in the second direction and prohibit movement in the first direction.

5 Claims, 14 Drawing Sheets

U.S. PATENT DOCUMENTS

| | | | |
|---|---|---|---|
| 5,630,832 A | 5/1997 | Giordano et al. | |
| 5,665,100 A | 9/1997 | Yoon | |
| 5,735,849 A | 4/1998 | Baden et al. | |
| 5,746,759 A | 5/1998 | Meade et al. | |
| 5,782,747 A | 7/1998 | Zimmon | |
| 5,797,936 A | 8/1998 | Kleihues | |
| 5,797,939 A | 8/1998 | Yoon | |
| 5,797,958 A | 8/1998 | Yoon | |
| 5,820,009 A | 10/1998 | Melling et al. | |
| 5,827,323 A | 10/1998 | Klieman et al. | |
| 5,836,960 A | 11/1998 | Kolesa et al. | |
| 5,893,835 A | 4/1999 | Witt et al. | |
| 5,893,863 A | 4/1999 | Yoon | |
| 5,908,420 A | 6/1999 | Parins et al. | |
| 5,984,938 A | 11/1999 | Yoon | |
| 5,984,939 A | 11/1999 | Yoon | |
| 6,017,358 A | 1/2000 | Yoon et al. | |
| 6,024,741 A | 2/2000 | Williamson, IV et al. | |
| 6,024,744 A | 2/2000 | Kese et al. | |
| 6,117,158 A | 9/2000 | Measamer et al. | |
| 6,162,209 A | 12/2000 | Gobron et al. | |
| 6,214,028 B1 | 4/2001 | Yoon et al. | |
| 6,299,625 B1 | 10/2001 | Bacher | |
| 6,358,268 B1 | 3/2002 | Hunt et al. | |
| 6,391,043 B1 | 5/2002 | Moll et al. | |
| 6,425,896 B1 | 7/2002 | Baltschun et al. | |
| 6,506,208 B2 | 1/2003 | Hunt et al. | |
| 6,602,252 B2 | 8/2003 | Mollenauer | |
| 6,730,109 B2 | 5/2004 | Wöllmer | |
| 6,773,434 B2 | 8/2004 | Ciarrocca | |
| 6,773,444 B2 | 8/2004 | Messerly | |
| 6,814,745 B2 | 11/2004 | Prestel | |
| 6,976,992 B2 | 12/2005 | Sachatello et al. | |
| 7,087,070 B2 | 8/2006 | Flipo | |
| 7,090,673 B2 | 8/2006 | Dycus et al. | |
| 7,150,749 B2 | 12/2006 | Dycus et al. | |
| 7,208,005 B2 | 4/2007 | Frecker et al. | |
| 7,331,978 B2 | 2/2008 | Haluck | |
| 2001/0005787 A1 | 6/2001 | Oz et al. | |
| 2003/0065358 A1* | 4/2003 | Frecker et al. | 606/205 |
| 2004/0243176 A1 | 12/2004 | Hahnen et al. | |
| 2005/0021079 A1* | 1/2005 | Kalmann et al. | 606/205 |
| 2005/0143774 A1 | 6/2005 | Polo | |
| 2006/0025811 A1 | 2/2006 | Shelton | |
| 2006/0025812 A1 | 2/2006 | Shelton | |
| 2006/0074416 A1 | 4/2006 | Hushka | |
| 2006/0190031 A1 | 8/2006 | Wales et al. | |
| 2007/0027468 A1 | 2/2007 | Wales et al. | |
| 2007/0106297 A1 | 5/2007 | Dumbauld et al. | |
| 2007/0173814 A1* | 7/2007 | Hixson et al. | 606/51 |
| 2007/0179525 A1 | 8/2007 | Frecker | |
| 2007/0213706 A1 | 9/2007 | Dumbauld et al. | |
| 2007/0250048 A1 | 10/2007 | Gobron | |

FOREIGN PATENT DOCUMENTS

| | | |
|---|---|---|
| WO | WO9405224 | 3/1994 |

* cited by examiner

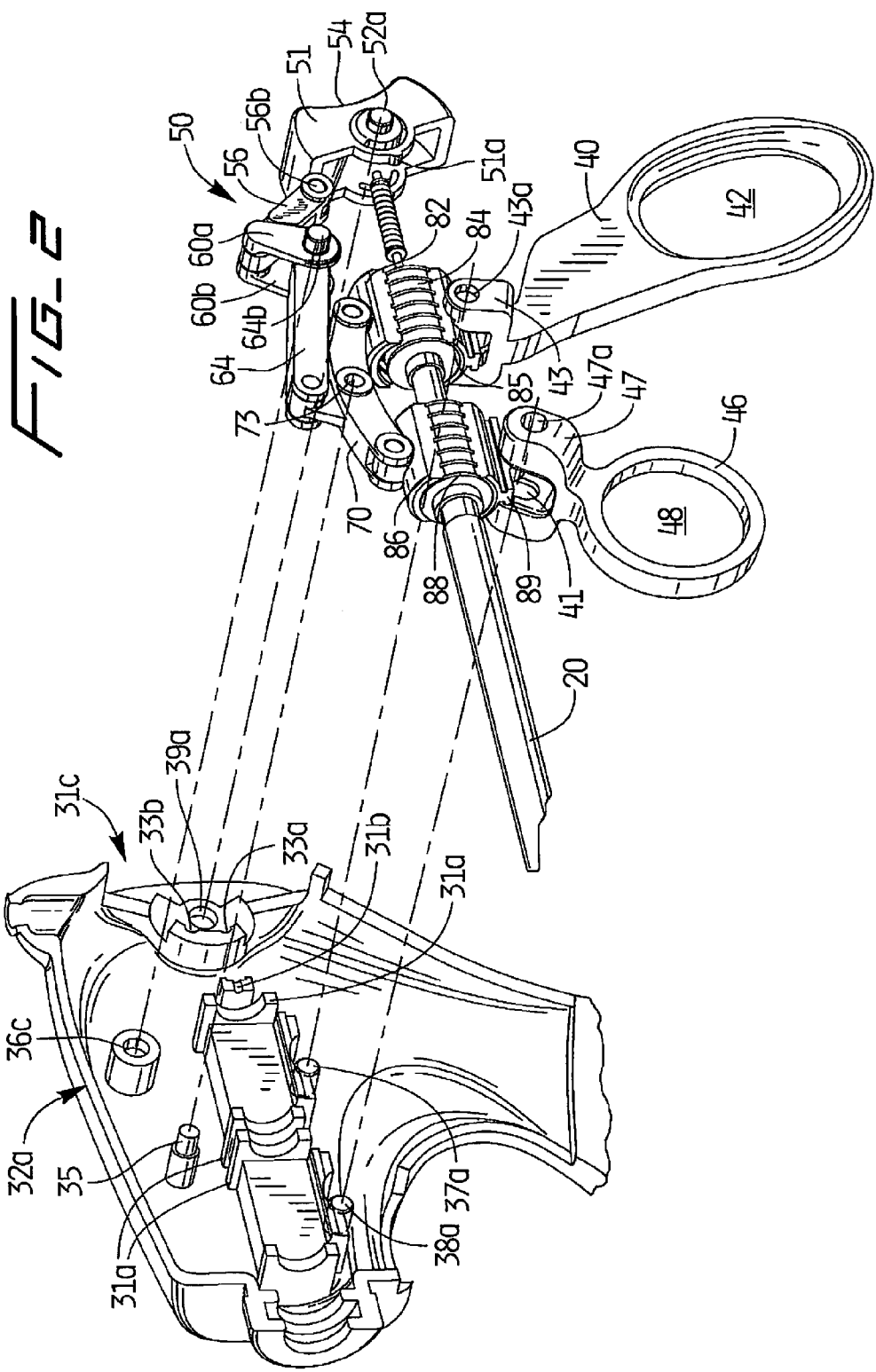

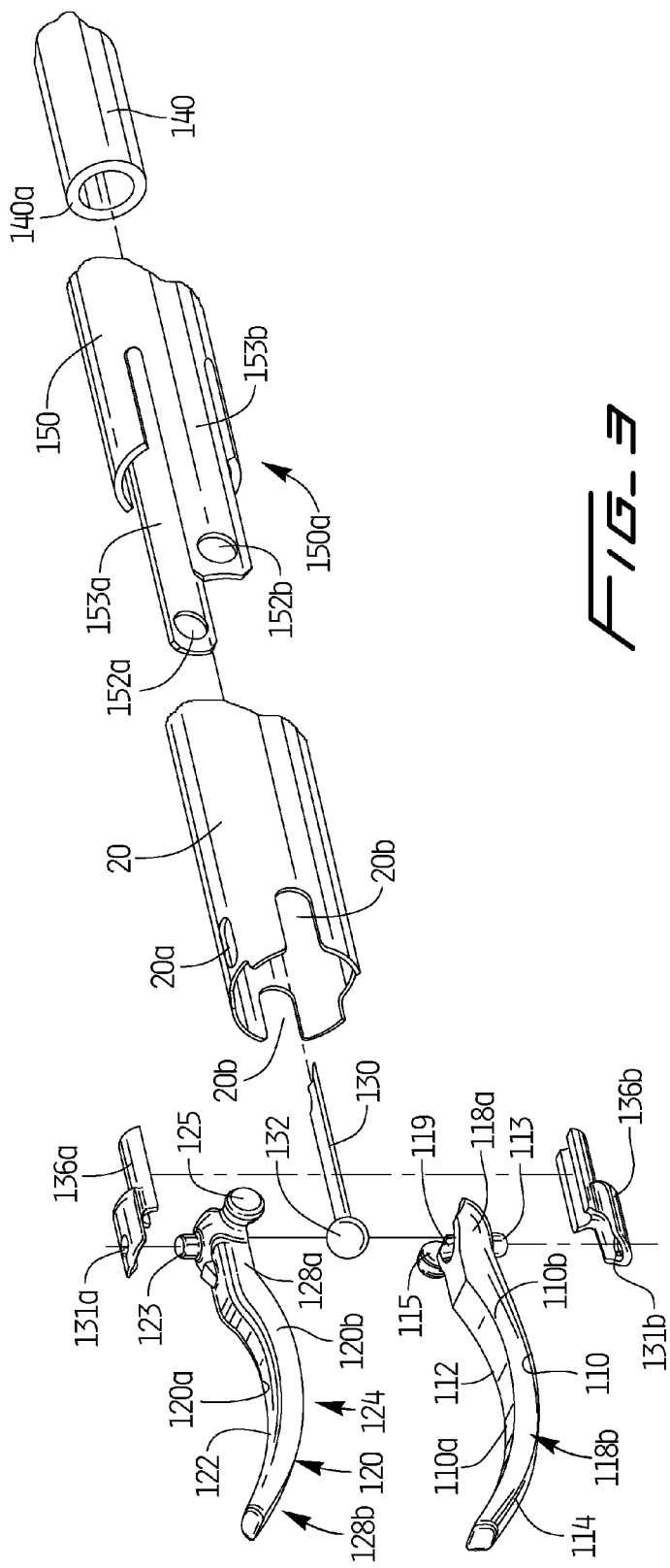

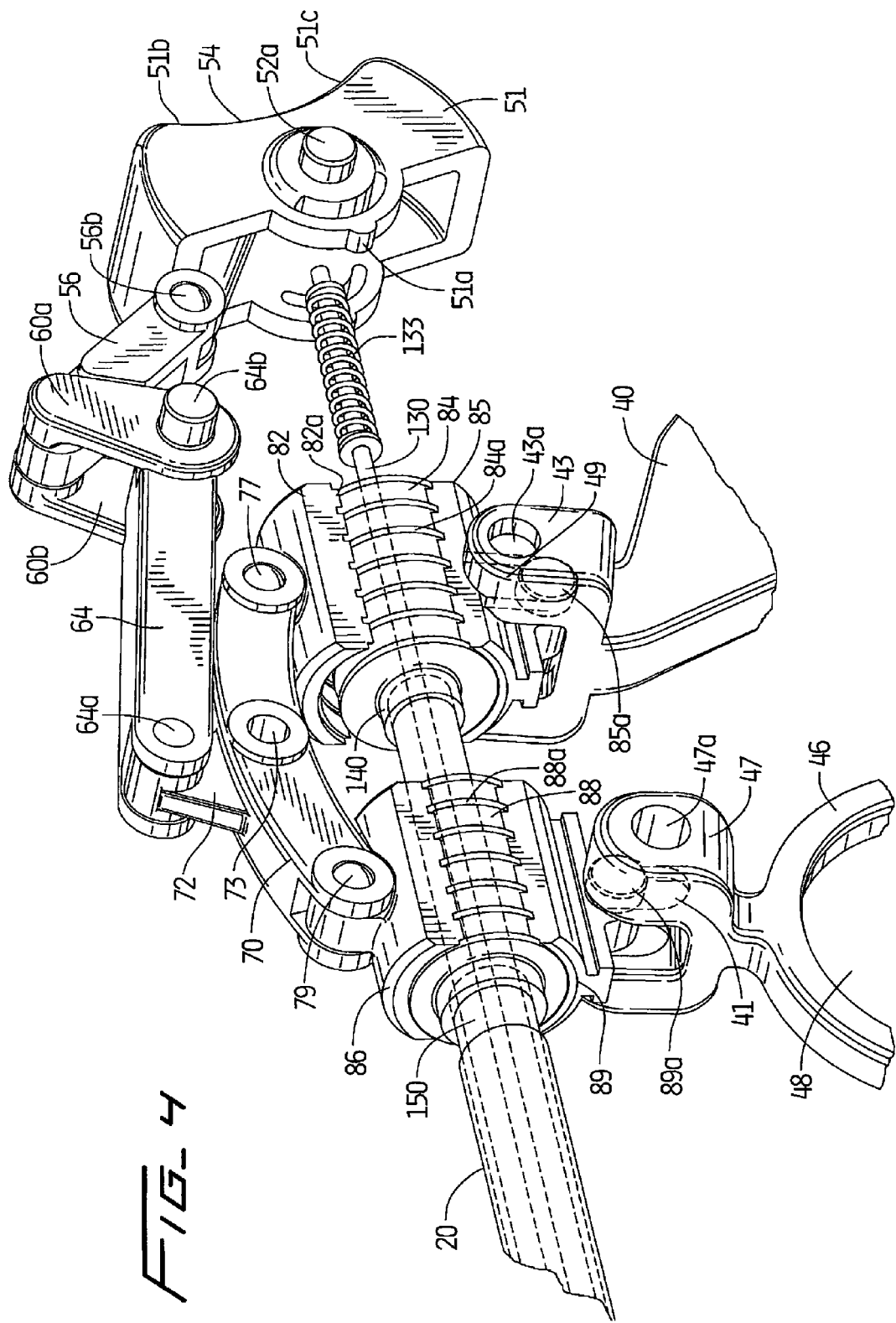

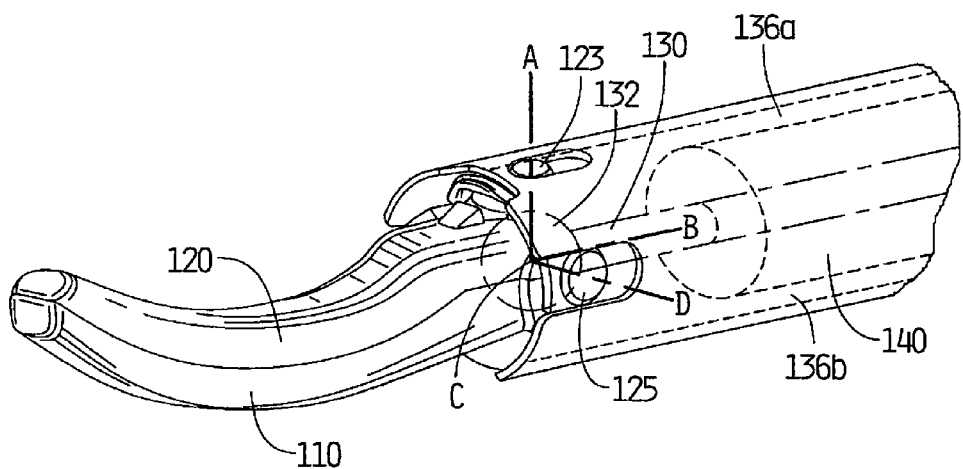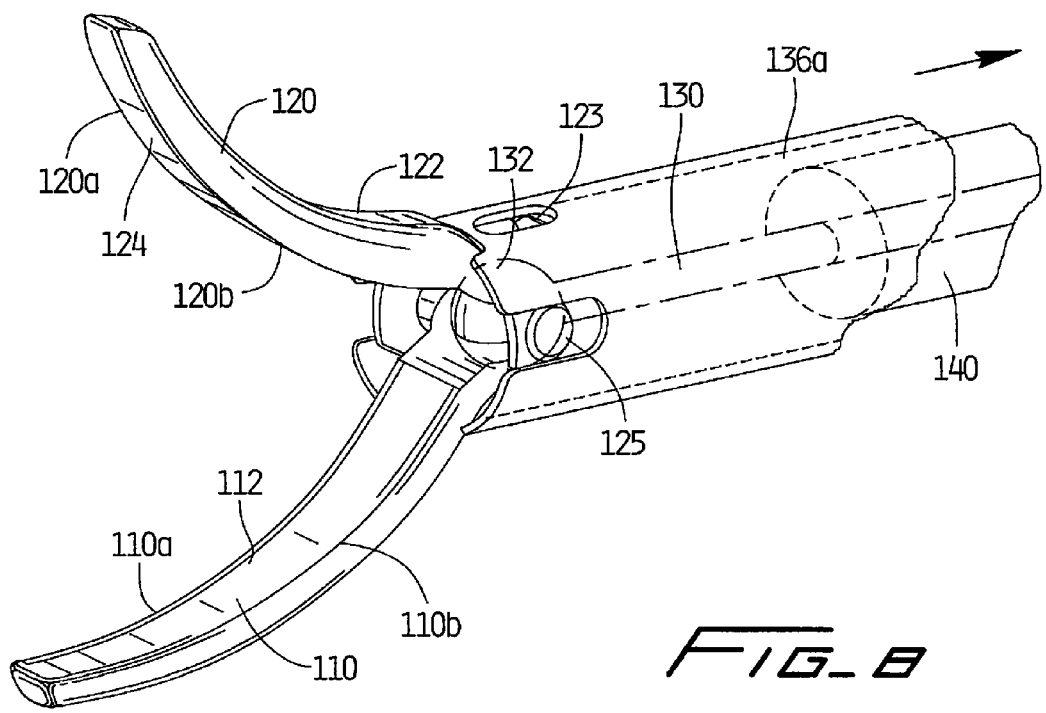

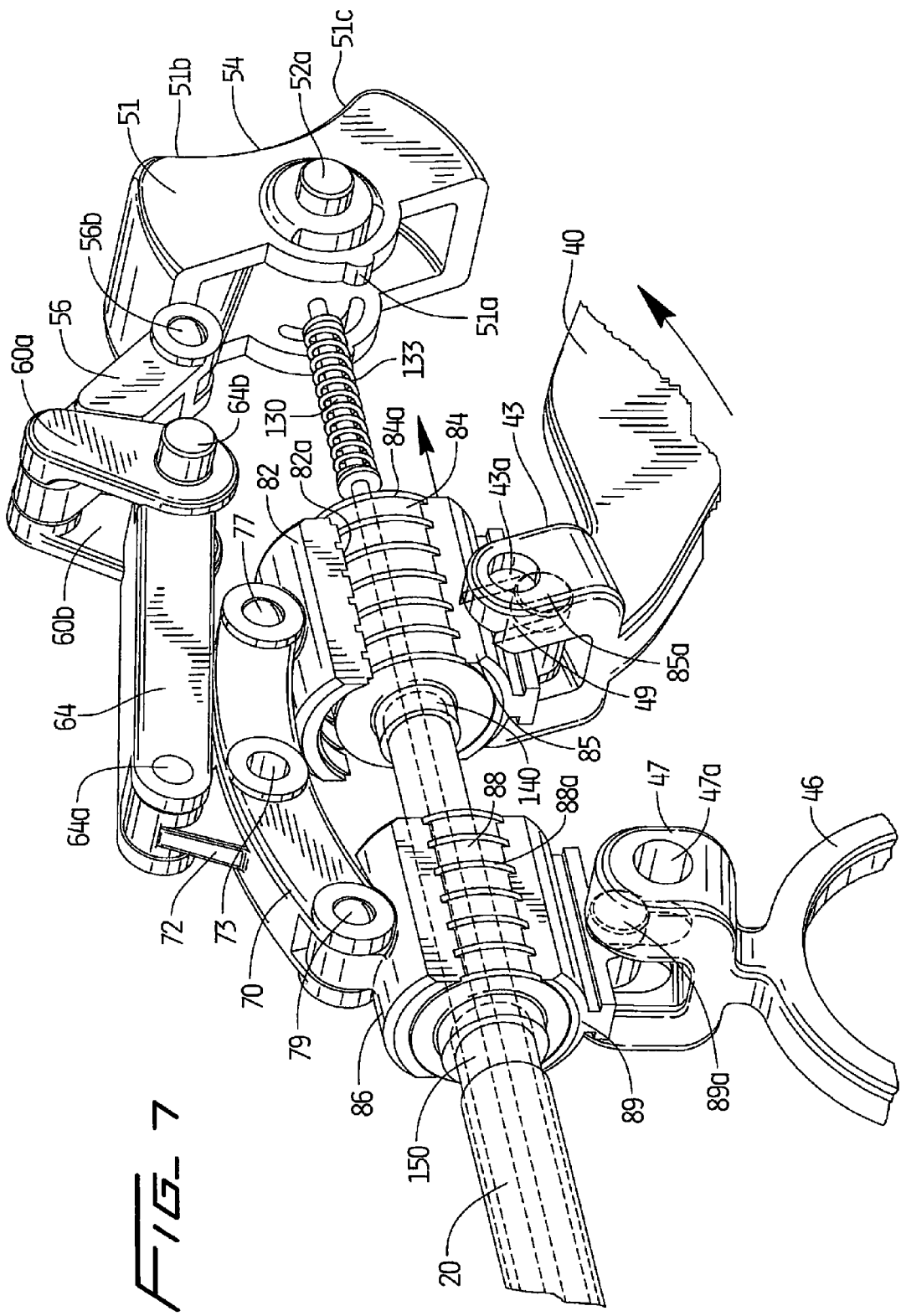

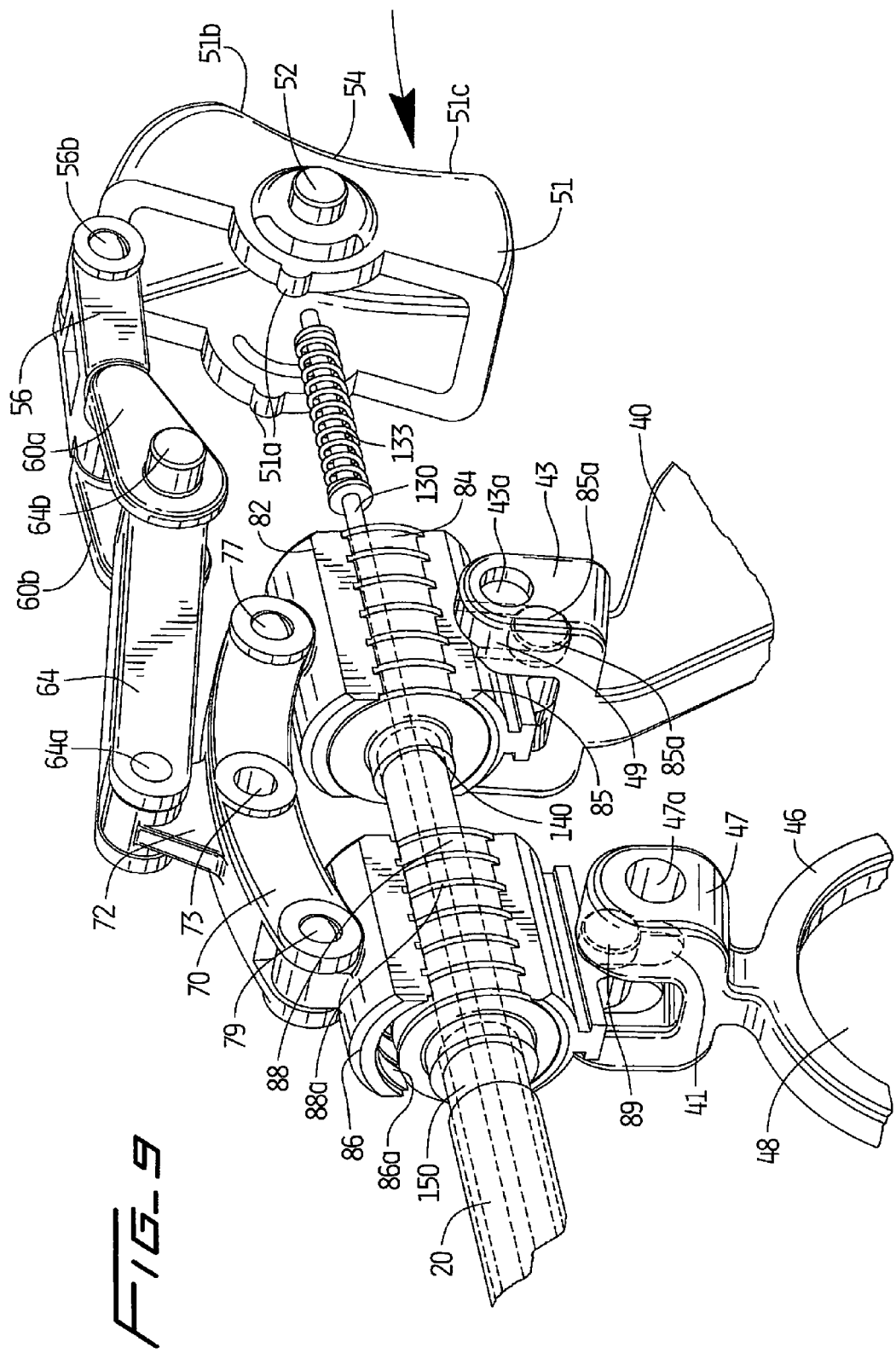

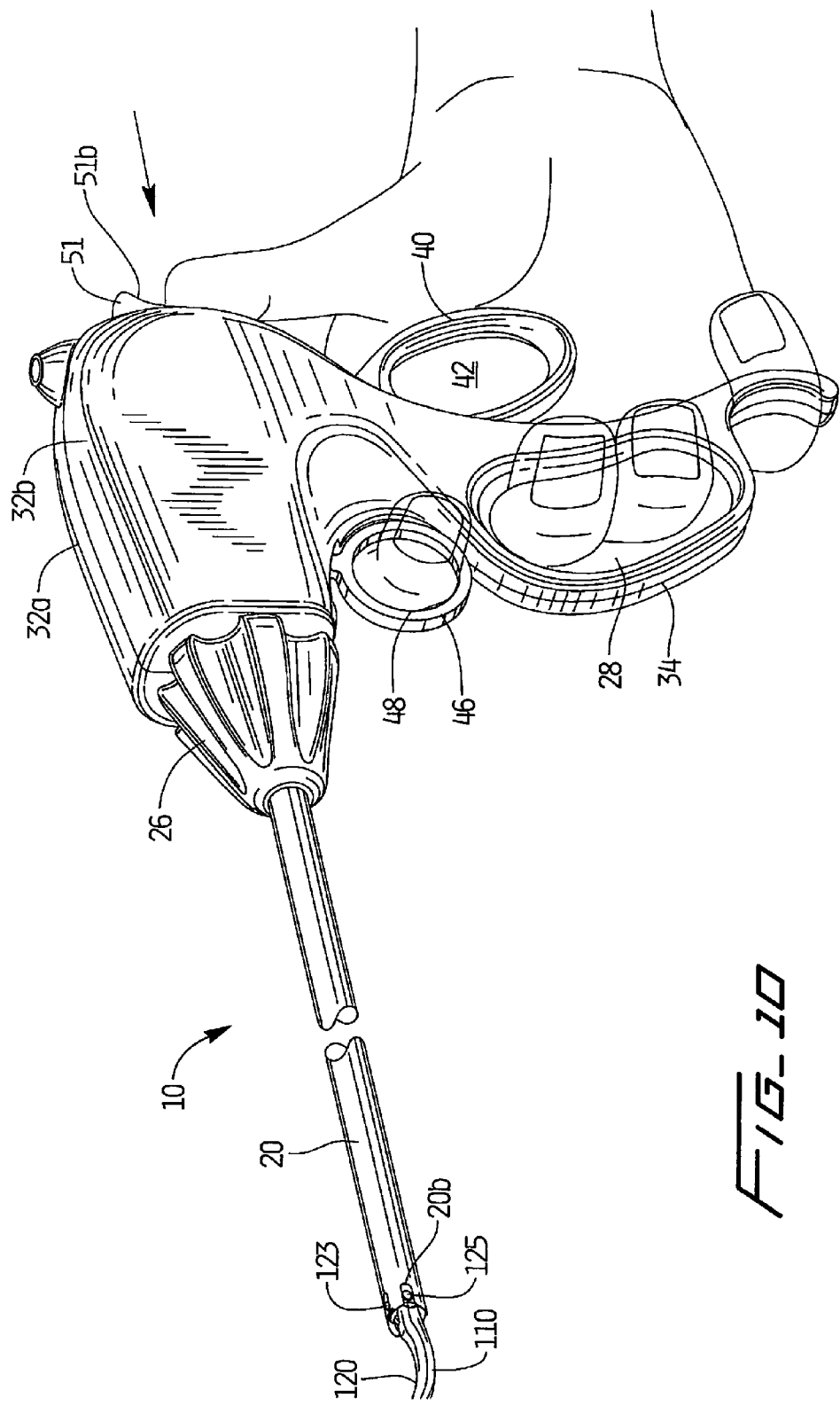
FIG_10

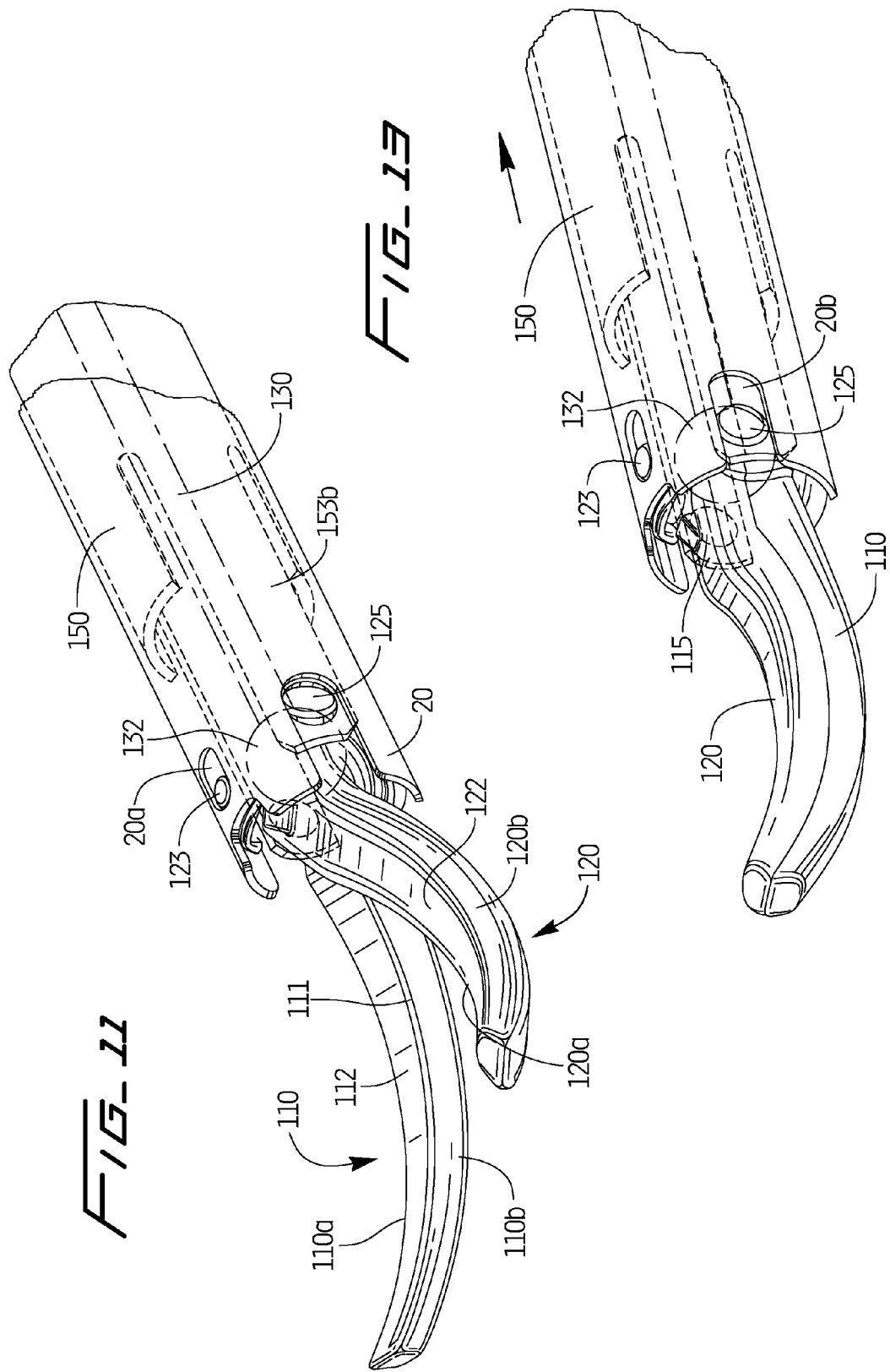

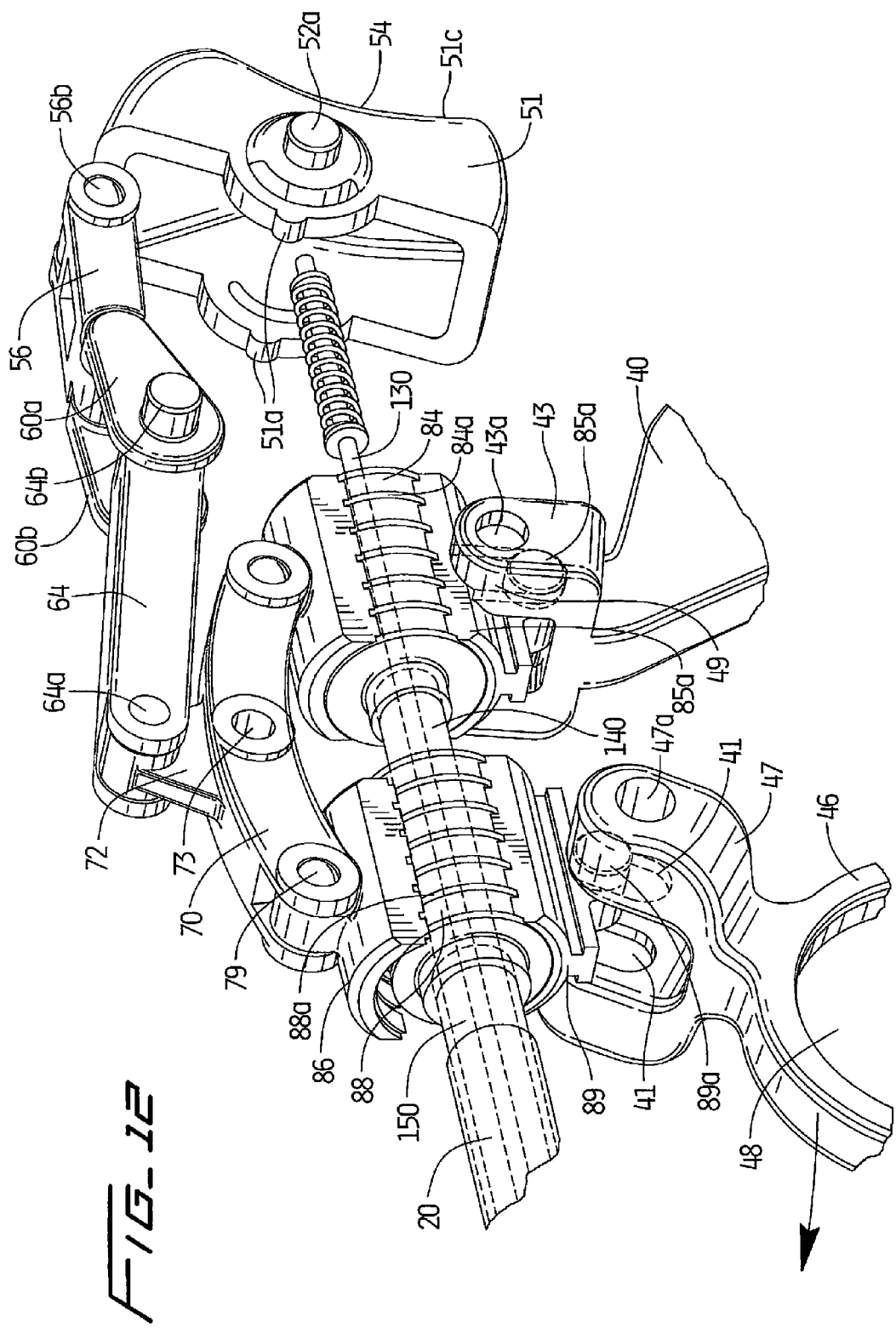

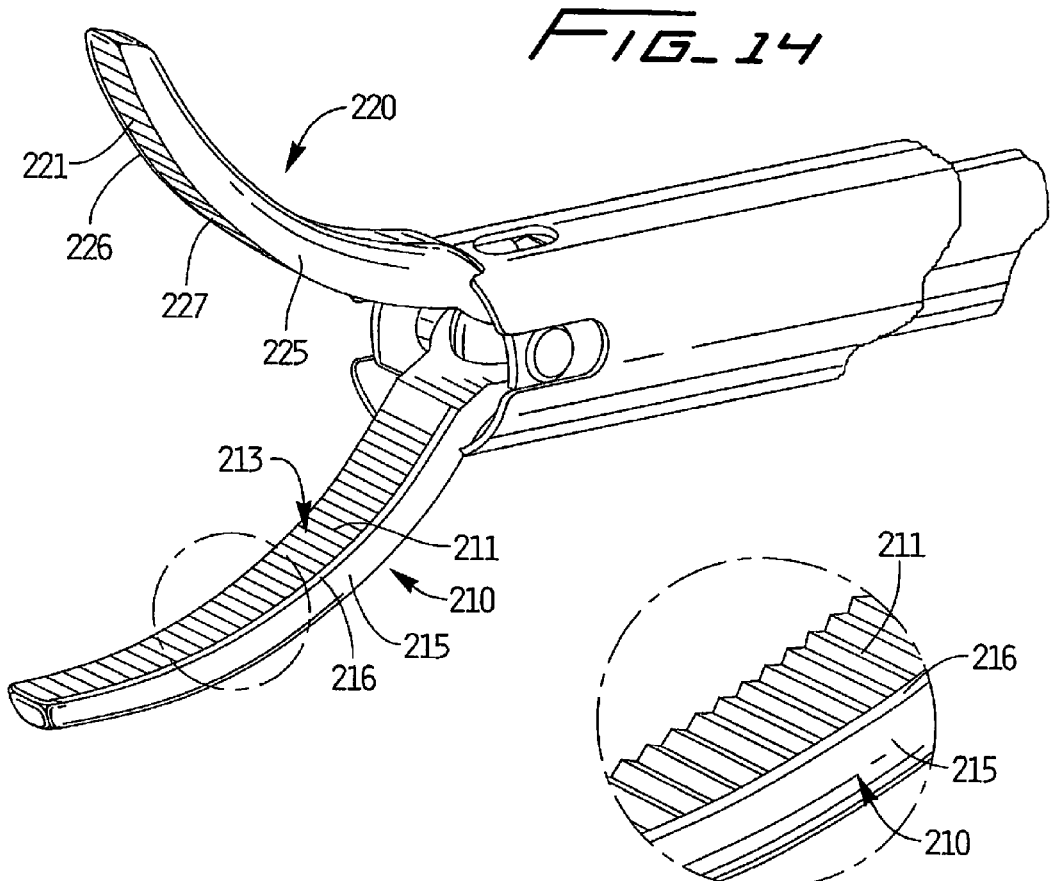
FIG_14
FIG_14A
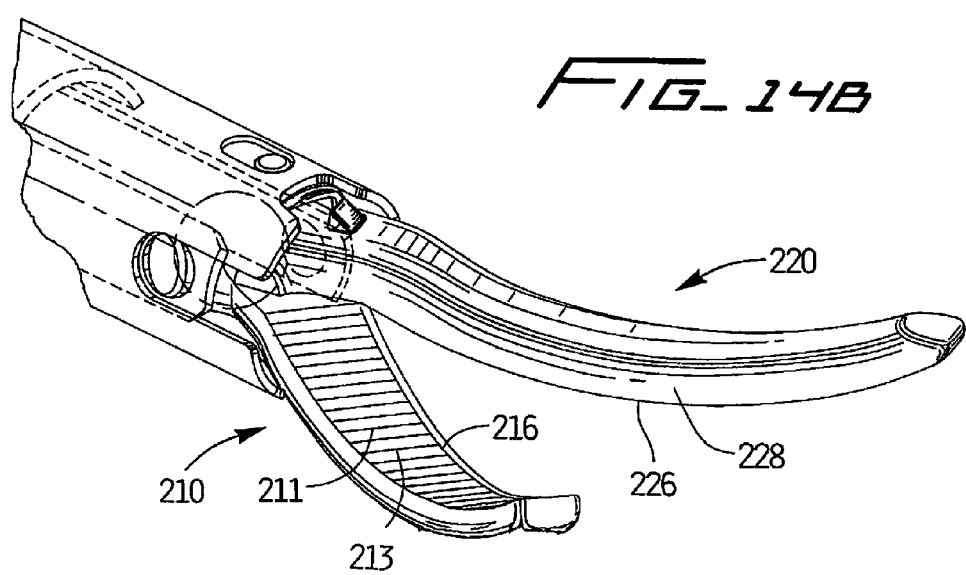
FIG_14B

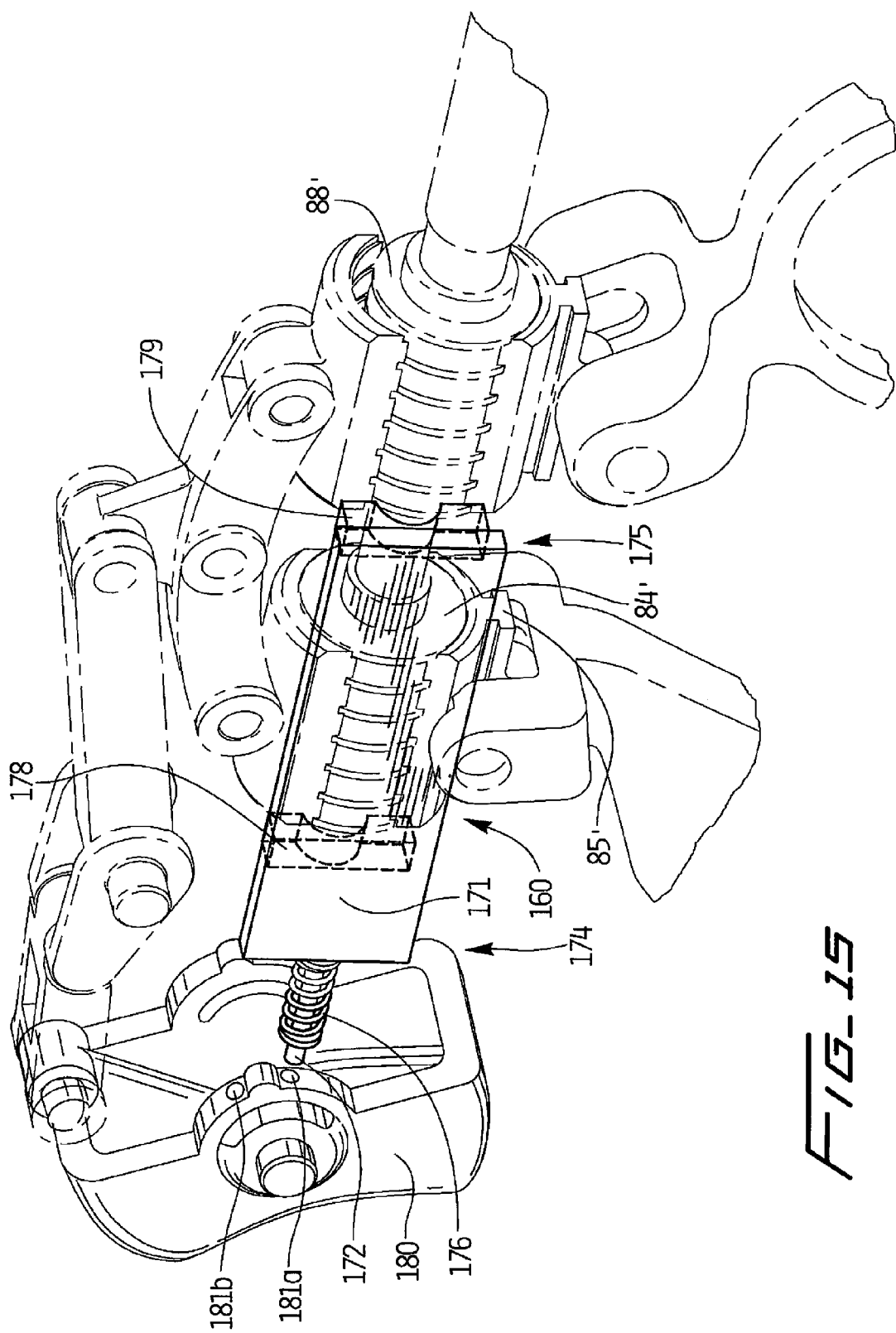

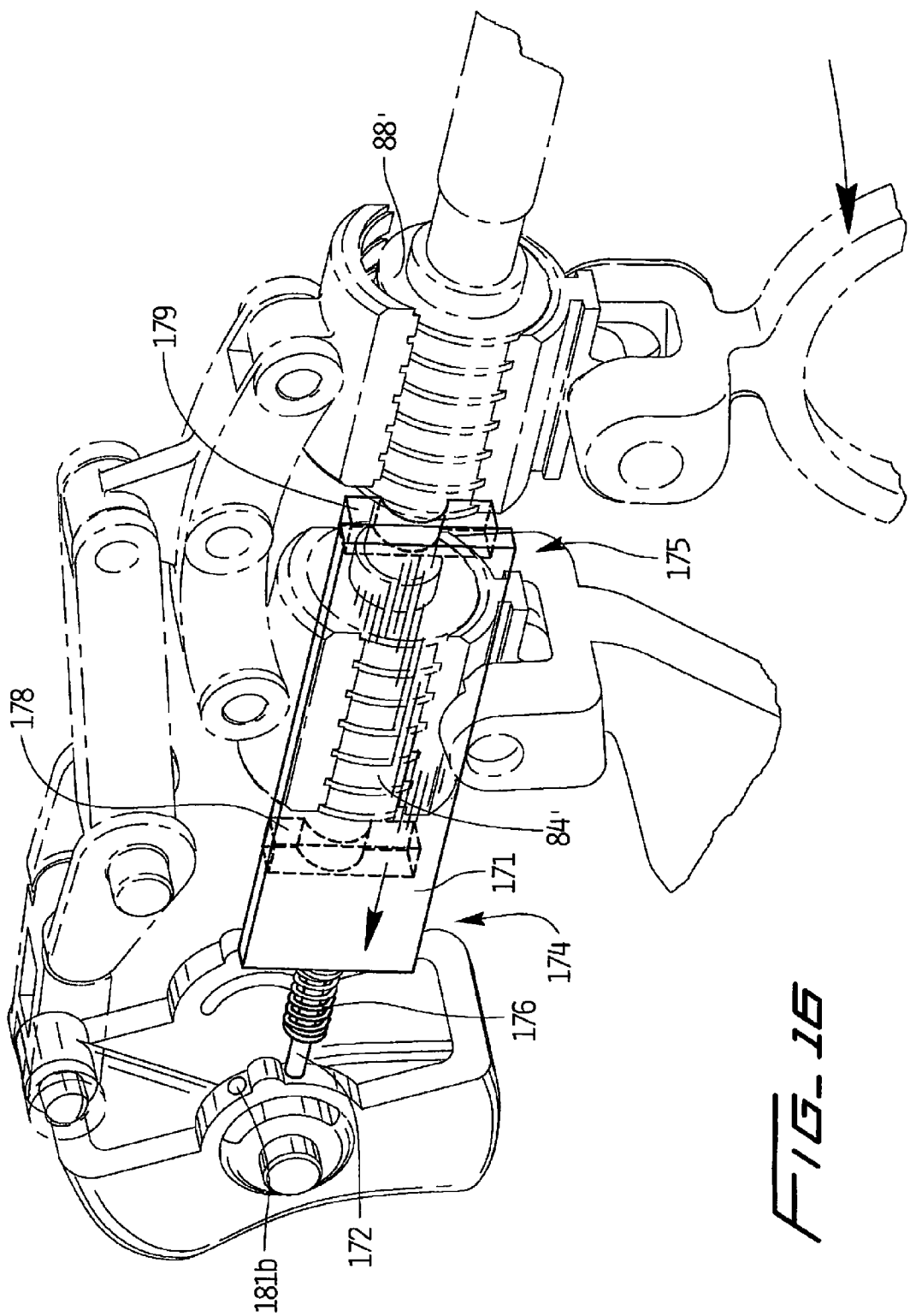
FIG._16

SURGICAL INSTRUMENT FOR GRASPING AND CUTTING TISSUE

This application claims priority from provisional patent application Ser. No. 61/066,063, filed Feb. 15, 2008, the entire contents of which is incorporated herein by reference.

BACKGROUND OF THE INVENTION

1. Field of the Invention

This application relates to a surgical instrument and more particularly to a surgical instrument for both grasping and cutting tissue.

2. Background

In minimally invasive surgery, the surgical procedure is performed by access to the surgical site through one or more small incisions. The surgical site is visualized by an endoscope inserted through one of the incisions and various surgical instruments are inserted through the incisions to manipulate the tissue as desired. The advantages of minimally invasive surgery are well established which include improved cosmesis, reduced chance of infection, faster patient recovery time and lower hospital costs.

Minimally invasive surgical procedures typically require the tissue to be grasped and held or manipulated. These procedures also typically require the tissue to be severed. Currently, to perform cutting and grasping functions separate instrumentation is required. This results in the time consuming task of withdrawing one of the instruments from the incision (usually through an access port such as a trocar extending into the patient) and inserting another instrument through the port. Not only does this take up valuable surgical time, but there is an increased chance of infection by passage of the instruments outside the body. There is also the risk of damaging tissue as the second instrument is inserted and advanced to the surgical site.

In these minimally invasive procedures, oftentimes the grasper jaws are used to dissect tissue. This can be achieved by opening the jaws to dissect the tissue with their outer portion to create a working space for access to the surgical site. During this dissection and instrument advancement, a vessel may be encountered which requires severing to provide further access to the surgical site. The surgeon sometimes cauterizes the vessel to sever it, but such "excessive cauterization" could damage surrounding tissue. Another alternative utilized by the surgeon is to remove the grasper and insert a pair of scissors or shears to sever the vessel. This instrument exchange has the disadvantages enumerated above. Additionally, after severing, to continue dissection, the scissors would have to be removed and a grasper reinserted. If another vessel requires cutting, an exchange for a scissor would again be necessary. As can be appreciated, multiple instrument exchanges could occur, thereby multiplying the foregoing risks. Some surgeons might try to use the open scissor jaws for dissection, but there is a risk of inadvertent cutting of tissue, so exchanging for a grasper is preferred.

Another example where currently instrument exchange between a scissor and grasper is necessary is in laparoscopic cholecystectomy. In this procedure, typically open jaws of the grasper are used to dissect around the bile duct and then a clip applier extending through a different access opening applies one or more clips on each side of the target area of the duct. The surgeon then needs to remove the grasper and insert a scissor to cut between the clips. Next, the scissors need to be removed so that graspers can be inserted to remove the gall bladder. As can be appreciated, exchanges of the grasping and cutting instrument are required.

It would be advantageous to provide a single instrument which achieves both cutting and grasping which would thereby avoid the disadvantages enumerated above of instrument exchanges. This was recognized in U.S. Pat. Nos. 6,391,043 and 7,410,494, commonly owned with the present application. However, there are several disadvantages associated with the instruments of these two patents. The present invention advantageously overcomes the disadvantages of these instruments and provides an instrument for both cutting and grasping tissue which provides significant manufacturing and clinical advantages.

SUMMARY OF THE INVENTION

The present invention provides an instrument capable of both cutting (severing) tissue and grasping tissue using the same pair of jaws. The instrument may also advantageously have a uniquely designed ergonomic handle assembly which eases manipulation of the instrument jaws. The instrument may also advantageously have a safety to ensure the jaws are in their closed position when they are switched between the cutting and grasping functions. Still further, the instrument may further advantageously have a built in mechanism to prevent movement of the jaws in a cutting action when a grasping action is selected and prevent movement of the jaws in a grasping action when a cutting action is selected.

The present invention provides in one aspect a surgical instrument for cutting and grasping tissue comprising a handle assembly disposed at a proximal portion of the instrument, an elongated member extending from the handle assembly, a first jaw positioned adjacent a distal portion of the elongated member, and a second jaw positioned adjacent the distal portion of the elongated member and mounted for movement with respect to the first jaw. A first movable member is operably associated with the second jaw and is movable between first and second positions to move the second jaw in a first direction about a first pivot axis in a grasping action. A second movable member is operably associated with the second jaw and movable between first and second positions to move the second jaw in a second direction different than the first direction and about a second pivot axis in a cutting action. A switch is positioned at the proximal portion of the instrument and a selecting member is actuated by movement of the switch. The selecting member is movable between a first position to enable movement of the second jaw in the first direction and prohibit movement in the second direction and a second position to enable movement of the second jaw in the second direction and prohibit movement in the first direction.

Preferably, the instrument further comprises first and second locking mechanisms wherein the selecting member comprises a rotatable linking member movable for selective engagement of one of the first and second locking mechanisms.

In a preferred embodiment the instrument includes a first gear operably associated with the first movable member, a second gear operably associated with the second movable member, a first locking member engageable with the first gear and a second locking member engageable with the second gear, the selecting member selectively moving one of the first and second locking members into engagement with its respective gear.

In a preferred embodiment, the first jaw has a first upper surface with a first edge and a second edge and the second jaw has a second lower surface with a third edge and a fourth edge, wherein in a cutting action, the first and third edges pass each other in substantially parallel planes and in a grasping action the first and third edges pivot away from each other in transverse planes. In a preferred embodiment, the first pivot axis and the second pivot axes intersect and are substantially perpendicular The instrument may include a linkage mechanism having multiple links linking the switch to the selecting member.

In a preferred embodiment, the instrument may include a safety mechanism operably associated with the switch to prevent movement of the switch if the jaws are not in a closed position.

In a preferred embodiment, both the first jaw and second jaws are movable by the movable members.

In a preferred embodiment, a first handle is operably associated with the first movable member, a second handle is operably associated with the second movable member, and the first movable member comprises a first tubular member and the second movable member comprises a second tubular member, the tubular members preferably being coaxial.

In another aspect, the present invention provides a surgical instrument for cutting and grasping tissue comprising an elongated member, a first jaw positioned adjacent a distal portion of the elongated member, and a second jaw positioned adjacent the distal portion of the elongated member and mounted for movement with respect to the first jaw. A first movable member is operably associated with the second jaw and is movable between first and second positions to move the second jaw in a first direction in a grasping action. A second movable member is operably associated with the second jaw and is movable between first and second positions to move the second jaw in a second direction different than the first direction in a cutting action. A switch is positioned at a proximal portion of the instrument. A handle assembly includes a stationary grip, a first actuator and a second actuator, wherein the first actuator is operably associated with the first movable member to move the second jaw in a grasping action and the second actuator is operably associated with the second movable member to move the second jaw in the cutting action.

In one embodiment, the first actuator is positioned proximal of the stationary grip and the second actuator is positioned distal of the stationary grip.

In a preferred embodiment, the first actuator is operably associated with a first gear mechanism and the second actuator is operably associated with a second gear mechanism.

In a preferred embodiment, the switch is movable between first and second positions, wherein in the first position the switch enables movement of the second jaw in the first direction and prohibits movement in the second direction and in the second position the switch enables movement of the second jaw in the second direction and prohibits movement in the first direction. In a preferred embodiment, first and second locking elements are operably associated with the switch to prohibit movement of the first or second actuator, depending on the position of the switch.

In another aspect, the present invention provides a surgical instrument for performing first and second different functions on tissue comprising an elongated member, a first jaw positioned adjacent a distal portion of the elongated member, and a second jaw positioned adjacent the distal portion of the elongated member and mounted for movement with respect to the first jaw. The first and second jaws are movable between open and closed positions in a first orientation and are further movable between open and closed positions in a second different orientation. A first actuating mechanism moves the jaws in the first orientation and a second actuating mechanism moves the jaws in the second orientation. A switch is provided for choosing the first or second actuating mechanism, wherein the switch can be activated only when the jaws are in the closed position.

In one embodiment, the first function is cutting and the second function is grasping. In this embodiment, preferably the first jaw has a first upper surface with a first edge and a second edge and the second jaw has a second lower surface with a third edge and a fourth edge, wherein when the jaws move between open and closed positions in the first orientation to perform the cutting function, the first and third edges pass each other in substantially parallel planes and when the jaws move between open and closed positions in the second orientation in the grasping function, the first and third edges pivot away from each other in transverse planes.

In one embodiment, movement of the switch moves a link in a clockwise or counterclockwise direction to effect operative engagement of one of the actuating mechanisms to prevent movement thereof.

The instrument may include a safety member operably associated with the switch, the safety member movable between a first position to lock the switch against movement and a second position to allow movement of the switch, the safety automatically locking the switch when the jaws are in the open position. In one embodiment, the safety includes a sliding member engageable with the switch in a proximal position.

In another aspect, the present invention provides a surgical instrument for performing first and second different functions comprising a handle assembly disposed at a proximal portion of the instrument, an elongated member extending from the handle assembly, a first jaw positioned adjacent a distal portion of the elongated member and a second jaw positioned adjacent the distal portion of the elongated member and mounted for movement with respect to the first jaw. A first movable member is operably associated with the second jaw and movable between first and second positions to move the jaws in a first direction about a first pivot axis to perform a first function on tissue. A second movable member is operably associated with the second jaw, the second movable member movable between first and second positions to move the jaws in a second direction different than the first direction and about a second pivot axis to perform a second different function on tissue. The second movable member is positioned within the first movable member. A switch is positioned at the proximal portion of the instrument to switch the instrument between the first and second functions.

In one embodiment, the first jaw has a first projecting member extending in a first direction engageable by the first movable member and a second projecting member extending in a second different direction engageable by the second movable member and the second jaw has a third projecting member extending in a first direction engageable by the first movable member and a fourth projecting member extending in a second different direction engageable by the second movable member. In one embodiment, the first and third projecting members lie substantially along the same axis and the second and fourth projecting members lie substantially along the same axis.

The present invention also provides in another aspect a handle assembly for a surgical instrument having first and second jaws. The handle assembly comprises a stationary handle, a first actuator, a second actuator and a switch. The first actuator has a first movable finger loop configured to receive a thumb of the user and is operably associated with a first movable member to effect movement of at least one of the instrument jaws in a grasping action. The second actuator has a second movable finger loop and is operably associated with a second movable member to effect movement of at least one of the instrument jaws in a cutting action. The first and second actuators and the switch are all operable by a single hand of a user, wherein the switch cannot be activated by the single hand of the user unless the user releases the thumb engagement of the first finger loop.

The handle assembly preferably further comprises a stationary handle positioned between the first and second actuators and having a third stationary finger loop.

The present invention also provides a surgical method of grasping and cutting tissue with a single instrument comprising:

providing an instrument having first and second jaws movable in a first orientation to perform a grasping function and movable in a second orientation to perform a cutting function;

moving a first actuator of the instrument to move the jaws in the first orientation between closed and open positions to grasp tissue;

moving a second actuator of the instrument to move the jaws in a second orientation between closed and open positions to cut tissue;

moving a switching mechanism between first and second positions to select the grasping or cutting function, wherein the switching mechanism can only be moved when the jaws are in the closed position.

In one embodiment, the step of moving the switching mechanism in the second position moves a first locking member into engagement with an advancing mechanism for moving the jaws in the first orientation. In one embodiment, the step of moving the switching mechanism in the first position moves a second locking member into engagement with an advancing mechanism for moving the jaws in the second orientation.

DETAILED DESCRIPTION OF THE DRAWINGS

Preferred embodiment(s) of the present disclosure are described herein with reference to the drawings wherein:

FIG. 2 is an exploded view of the handle assembly of the instrument of FIG. 1, showing one of the housing halves;

FIG. 3 is an exploded view of the jaw assembly and distal portions of the jaw actuators of the instrument of FIG. 1;

FIG. 4 is a perspective view of the actuators and switching mechanism corresponding to the position of the instrument of FIG. 1 and showing the switch in the grasping function position;

FIG. 5 is a perspective view of the jaws in the closed position corresponding to the position of the actuators of FIG. 4;

FIG. 7 is a view similar to FIG. 4 showing retraction of the grasper actuator to move the jaws to an open grasping position, and corresponding to the position of the instrument of FIG. 6;

FIG. 8 is a perspective view of the jaws in the grasper open position corresponding to the actuator position of FIGS. 6 and 7;

FIG. 9 is a perspective view similar to FIG. 4 showing the switching mechanism in the cutting function position and the jaws in the closed position, and further showing the grasper spur gear locking the grasper gear to prevent movement of the grasper handle;

FIG. 10 is a perspective view of the instrument similar to FIG. 6 showing the grasper handle in the at rest position to close the jaws and the switching mechanism moved to the cutting function position;

FIG. 11 is a perspective view of the jaws of the instrument of FIG. 1 in the open cutting position;

FIG. 12 is a view similar to FIG. 9 illustrating movement of the cutter handle to move the jaws to the closed position (the switch remaining in the cutting function position);

FIG. 13 is a perspective view of the jaws in the closed position after movement from the open position of FIG. 11 in a scissors action;

FIG. 14 is a perspective view of an alternate embodiment of the jaws having a series of teeth and a raised cutting surface;

FIG. 14A is a close up view of the area of detail of FIG. 14;

FIG. 14B is a perspective view similar to FIG. 14 showing the other side of the jaw assembly;

Figure 1:
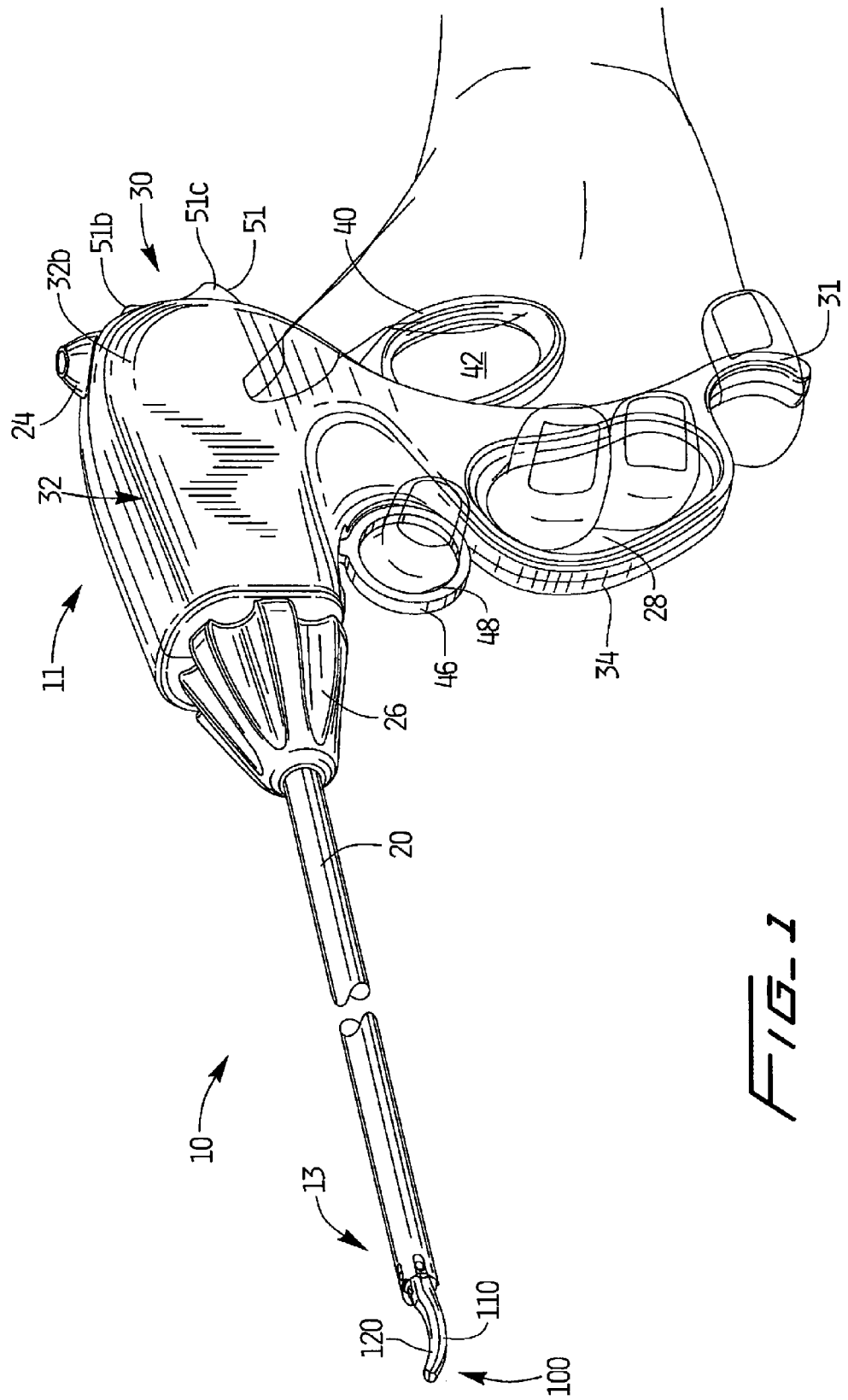
FIG. 1 is a perspective view of a first embodiment of the surgical instrument of the present invention showing the grasper handle and the cutting handle in the at rest position with the jaws in the closed position.

FIG. 15 is a perspective view of an alternate embodiment of the instrument of the present invention having a locking plate to prevent movement of the switching mechanism if the jaws are not in the closed position, the locking plate shown in the nonengaged position to allow movement of the switch; and FIG. 16 is a perspective view similar to FIG. 15 showing the locking plate in the engaged position to prevent movement of the switch from the cutting function position to the grasping function position.

DETAILED DESCRIPTION OF PREFERRED EMBODIMENTS

Turning now to the drawings, wherein like reference numerals identify similar or like components throughout the several views, a surgical instrument is designated generally by reference numeral 10. Throughout the description, the term "proximal" will refer to the portion of the instrument closer to the user and the term "distal" will refer to the portion of the instrument further from the user.

Turning first to FIG. 1, the surgical instrument 10 has a handle assembly 30 at its proximal portion 11, an elongated member or shaft 20 extending distally from the handle assembly 30 and a jaw assembly 100 at the distal portion 13. The jaw assembly 100 includes a first jaw 110 and a second jaw 120 which are operably connected to the handle assembly 30. In the orientation of FIG. 1, the first jaw 110 forms the lower jaw and the second jaw 120 forms the upper jaw. A rotating knob 26 adjacent the handle assembly 30 and at a proximal region of the elongated shaft (outer tube) 20 rotates the shaft 20 and thereby the jaws 110, 120 of the instrument 10 about a longitudinal axis of the shaft 20. A rocker switch 51 of switching mechanism 50 (FIG. 2) enables switching between a grasping and cutting function of the jaws 110, 120 as described in more detail below. A receptacle 34 for a conventional monopolar cautery plug optionally extends from the top of the body of handle assembly 30.

The jaws 110, 120 are movable in a first orientation to perform a cutting function and movable in a second different orientation to perform a grasping function. Thus, the jaws move in different planes to cut (sever) tissue and to grasp tissue. More specifically, in a grasping action, jaws 110 and 120 pivot about a first pivot axis in planes at acute angles to each other so the upper surface 112 of lower jaw 110 and the lower surface 124 of upper jaw 120 move away from each, forming an acute angle in the open position. Stated another away, the opposing edges or walls 110a, 110b of jaw 110 and opposing edges 120a, 120b of jaw 120 to move downwardly and upwardly, respectively, away from each other. This is depicted in FIGS. 5 and 8 wherein the jaws 110, 120 are shown in FIG. 5 in a closed configuration and in FIG. 8 in an open grasping position.

In a cutting action, the first and second jaws 110, 120 pivot about a second pivot axis such that the upper surface 112 of jaw 110 and lower surface 124 of jaw 120 move away from each other in substantially parallel planes in a scissor-like action. In this manner, edge 110b of lower jaw 110 which has a sharpened surface 111 interacts with an edge of upper jaw 120 opposite edge 120b which has a sharpened surface. This is shown in FIGS. 11 and 13 wherein the jaws 110, 120 are shown in the open and closed positions, respectively. When moved to the closed position, the sharpened surface 111 on edge 110b of lower jaw 110 passes by the sharpened surface on the lower edge of upper jaw 120. (Note this sharpened edge of upper jaw 120 is not visible in FIG. 11 as it is opposite edge 120b; however the sharpened edge is shown in the upper jaw of the alternate embodiment of FIG. 14 discussed below).

As shown in FIG. 5, the first and second pivot axes, i.e. axis D about which the jaws 110, 120 move in the grasping orientation and axis A about which the jaws move in a cutting orientation, intersect a center point C and are preferably substantially perpendicular.

Although both jaws are shown and described as moving in the cutting and grasping action, it is also contemplated that alternatively only one of the jaws could move in the grasping action and/or cutting action with the other jaw remaining fixed. Therefore relative movement of the jaws as used herein refers to one of the jaws moving with respect to the other fixed jaw or both of the jaws 110, 120 moving between their various positions.

With reference to FIG. 3, a lower projecting member or pin 113 extends from the lower surface 114 of lower jaw 110 and is configured to engage opening 131b in yoke half 136b for movement of the jaw 110 in a grasping action (FIG. 8). A side projecting member or pin 115 engages the cutter tube 150 (described below) for movement of the jaw 110 in a cutting action (FIG. 11).

Lower jaw 110 has a proximal upper recess 119, preferably substantially hemi-spherical as shown to receive a ball 132 of shaft 130. The shaft 130 and ball 132 are held in tension by tension spring 133 (see e.g. FIG. 4) to remove the tolerances, i.e. reduce the play of the jaws. Jaw 110 also has a linear region 118a and an arcuate region 118b.

Upper jaw 120 is similar to lower jaw 110 and has an upper surface 122 opposite lower surface 124. An upper projecting member or pin 123 extends from the upper surface 122 and is configured to engage opening 131a in yoke half 136a for movement of the jaw 120 in a grasping action. A projecting member or side pin 125 engages the cutter tube 150 (described below) for movement of the jaws 110 in a cutting action. Note that side pins 115 and 125 extend from opposing sides of the jaw assembly 100. Preferably pins 113 and 123 lie substantially along the same axis and pins 115 and 125 lie substantially along the same axis.

Upper jaw 120 has a proximal lower recess similar to recess 119 of jaw 110, preferably substantially hemispherical, to receive ball 132 of shaft 130. Jaw 120 has a linear region 128a and an arcuate region 128b.

Preferably both jaws are movable, however, as noted above, it is also contemplated that one of the jaws could be fixed and the other movable. Also, other configurations of the jaws other than curved as shown are also contemplated. In the embodiment of FIG. 3, the jaws are shown with blunt tips Each of the jaws preferably has a series of teeth shown for example in the preferred alternate embodiment of FIG. 14. As shown, lower jaw 210 has teeth 211 on upper surface 213 and upper jaw 220 has teeth 221 on lower surface 227. Preferably the teeth 211, 221 extend substantially transversely to a longitudinal axis of the jaws 110, 120. The edge 215 of the lower jaw 210 has a raised rib 216 with a cutting surface. The upper jaw 220 has a raised rib 226 on its lower surface 227 of the edge 228 opposite edge 225 with a cutting surface to interact with the cutting surface of raised rib 216 when the jaws 210, 220 are moved in a scissor like fashion to sever tissue in the manner of FIGS. 11 and 13. The raised ribs 216 and 226 on the lower and upper jaws, respectively, illustratively extend beyond the plane of the respective teeth 211, 221 so as not to interfere with the scissors action of jaws 210, 220. In all other respects, including their configuration and actuation, jaws 210, 220 are identical to jaws 110 and 120 of FIG. 1.

The switching mechanism 50 for selectively locking the cutter or grasping gear mechanism of the instrument will now be described. With reference to FIGS. 2, 4, and 9, the switching mechanism 50 includes a rocker switch 51 positioned at a proximal portion of the instrument and having a pair of detents 51a engagable with a respective recess 33a or 33b in the housing 32 of handle assembly 30. A mounting pin 52a extends outwardly from each side of switch 51 and engages aperture 39a in housing half 32a and a similar aperture (not shown) in the other housing half 32b. Such mounting to the housing 32 provides for pivoting (rocking) movement of the switch 51. Note that only one of the housing halves, half 32a, is shown in FIG. 2; the other half 3b is not shown for clarity and is the mirror image of housing half 32a. Therefore only the mounting to housing half 32a will be described, it being understood that the components are mounted to housing half 32b in the same manner.

The detents 51a of switch 51 retain the rocker 51 in either a first position where the jaw grasping function is locked out or a second position where the jaw cutting function is locked out. This is achieved by engagement in either upper recess 33b of housing 32a (and housing 32b) for the cutting function or a lower recess 33a for the grasping function. The detents 51a can be retained in positions other than those shown e.g. a neutral position) and two or more detents can be provided and the detents can be provided in other parts of the switch. Other ways to retain the switch in its positions could also be provided. The switch 51 can include a curved indentation 54 which can have a knurled or irregular surface to facilitate actuation by the surgeon's thumb.

The switching mechanism 50 further includes a linkage mechanism operably associated with the rocker switch 51, best shown in FIGS. 2, 4 and 9. More specifically, the linkage mechanism includes a switch connecting link 56, a pair of rear (first) intermediate links 60a, 60b, a front (second) intermediate link 64, and a curved gear link 70. Link 56 is connected to an upper extension portion of rocker 51 via pin 56. Rear intermediate links 60a, 60b each have a pin for attachment to a front end of link 56. Rear intermediate links 60a, 60b are attached to a rear portion of front intermediate link 64 via pin 64b extending through opposing openings in link 64. Pin 64b is mounted within opening 36c in housing half 32a (as well as the other housing half 32b). The front intermediate link 64 has front holes aligned with the holes on extension 72 of curved link 70 for attachment to curved link 70 via pin 64a. Note in FIGS. 2, 4 and 7, the switching mechanism is in the grasping function position. In FIGS. 9 and 12, the switching mechanism is in the cutting function position.

A safety mechanism 160 is preferably provided to ensure the switching mechanism 50 cannot be activated unless the jaws 110, 120 are in the closed position. This is described in more detail below in connection with the alternate embodiment of FIG. 15.

Curved gear link 70 has a pair of rear holes and a pair of front holes to receive gear pins 77, 79, respectively. Central mounting holes 73 of link 70 receive housing pins 35 on each housing half 32a, 32b (or alternatively a single pin trapped between the housing halves) for movably (pivotably) mounting curved gear link 70 to the housing 32.

Curved link 70 moves in a rocker type fashion, pivoting about housing pin 35 connected in holes 73, preferably centrally disposed in link 70, to selectively engage one of the gear mechanisms. In this rocking movement, the curved link 70 moves between one position to effect engagement of the grasper gear mechanism and another position to effect engagement of a cutter gear mechanism, both described below.

The gear mechanism of the present invention provides a system for advancing the respective actuator tubes for opening and closing the jaws in a grasping or in a cutting function. The gear mechanism is also selectively lockable to lock movement of one of the actuator handles and respective actuator tubes while enabling movement of the other actuator handle and respective tube.

With continued reference to FIGS. 2, 4 and 7, the gear mechanism includes an upper grasper spur gear 82, lower grasper inverted spur gear 85 and a grasper gear 84. The gear mechanism further includes an upper cutter spur gear 86, inverted cutter spur gear 89 and cutter gear 88 positioned distally of the grasper gears 82, 84, and 85. As shown, preferably the teeth 84a, 88a of gears 84, 88 extend circumferentially.

The handle assembly is operably associated with the gears 84 and 88 such that movement of one of the handles moves the respective gears which in turn actuates a connected movable member, e.g. an actuator tube or shaft, to open and close the jaws. This is described in more detail below in connection with the discussion of the handle assembly.

The spur gears 82 and 86 of the gear mechanism 80 form locking mechanisms to selectively lock the respective gear 84, 88 against movement. In this manner, when a cutting action is desired, the rocker switch 51 is activated, i.e. manually actuated by the user to pivot about pivot pin 52a, to move the links of the switching mechanism 50 so that the teeth 82a of the grasper spur gear 82 mesh with the teeth 84a of grasper gear 84 to lock the grasper gear 84 against movement. This prevents movement of the grasper handle actuator 40 and is shown in FIGS. 9 and 12. When a grasping action is desired, the rocker switch 51 is activated to move the links of the switching mechanism 50 so that the teeth 86a of the cutter spur gear 86 mesh with the teeth 88a of the grasper gear 88 to lock the grasper gear 88 against movement. This prevents movement of the cutter handle actuator 46 and is shown in FIGS. 4 and 7.

More specifically, when the lower portion 51c of rocker switch 51 is pivoted toward the housing 32, link 56 is pulled back to pivot about pin 56b to a position more aligned with a longitudinal axis of the instrument as shown in FIG. 9. This in turn pivots rear intermediate links 60a, 60b to a position more aligned with the longitudinal axis of the instrument, thereby pulling front intermediate link 64 to pivot the rear portion of curved link 70 (via the connection pin 64a) downwardly so that cutter spur gear 86 is disengaged from cutter gear 88 and grasper spur gear 82 is engaged with grasper gear 84 to lock the gear 84 against sliding movement.

When the upper portion 51b of rocker switch 51 is pivoted toward the housing 50, link 56 is pivoted about pin 56b to a more angled position as shown in FIG. 4. This in turn pivots rear intermediate links 60a, 60b to a more angled position, thereby forcing a distal portion of front intermediate link 64 to move downwardly to pivot curved link 70 (via the connection pin 64a) counterclockwise so that grasper spur gear 82 is disengaged from grasper gear 84 and cutter spur gear 86 is engaged with cutter gear 88 to lock the gear 88 against sliding movement.

Turning now to the movable elements which operably connect the gears with the jaws, a grasper tube 140 and a cutter tube 150 are provided. More specifically and with reference to FIGS. 2, 3, 4 and 7, extending from grasper gear 84 is grasper tube 140. Grasper tube 140 is attached to yoke 136 (formed from yoke halves 136a, 136b) at its distal end 140a (see FIG. 3). When the grasper handle 40 is actuated to perform the grasping function, i.e. move the jaws 110, 120 from a closed position to an open position in the grasping orientation, grasper gear 84 is moved proximally from its distal position of FIG. 4 to its proximal position of FIG. 7, pulling attached grasper tube 140 and attached yoke 136 proximally. This moves the jaws 110, 120 from the closed position of FIG. 5 to the to the open grasping position of FIG. 8 due to the engagement of respective upper and lower pins 123, 113 of upper and lower jaws 120, 110 with respective openings 131a, 131b in yoke 136. That is, this pin engagement causes the jaws to pivot about axis "D" transverse to the longitudinal axis "B" of the jaws and instrument and passing through the side pins 125, 115. To close the jaws 120, 110, the grasper handle 40 is moved in the opposite direction (distally) back to its normal at rest position, thereby moving grasper gear 84 distally to thereby advance the grasper tube 140 and attached yoke 136 distally, forcing the jaws 120, 110 to pivot about axis "D" back to the position of FIG. 5. Note that outer tube (elongated member) 20 has slots 20a (FIG. 3) to accommodate pins 123, 113.

The grasper tube 140 is positioned inside and preferably coaxially with the cutter tube 150. Cutter tube 150 is slidably mounted within recesses formed in ribs 31 of housing half 32a and corresponding ribs on housing half 32b. (See FIG. 2). Cutter tube 150 is positioned within shaft 20.

Referring to FIGS. 3, 9 and 12, cutter tube 150 has a proximal end extending from cutter gear 88 and a distal end 150a. The distal end 150a has holes 152a, 152b on respective extensions 153a, 153b to receive side pins 115, 125 of jaws 110, 120, respectively. When the cutter handle 46 is actuated to perform the cutting function, i.e. move the jaws 110, 120 from a closed position of FIG. 13 outwardly to an open position of FIG. 11 in the cutting orientation, cutter gear 88 is moved proximally, pulling cutter tube 150 proximally from its distal position of FIG. 9 to its proximal position of FIG. 12. This moves the jaws 110, 120 to an open position due to the engagement of the holes 152a and 152b of extensions 153a, 153b with the side pins 115, 125. This causes the jaws 110, 120 to pivot about a cutting axis "A" extending transverse to the longitudinal axis of the jaws and instrument and passing through the upper and lower pins 123, 113. To close the jaws 110, 120 to cut tissue, the cutter handle 46 is moved in the opposite direction (proximally) to return to its at rest position, thereby moving cutter gear 88 distally to thereby advance the cutter tube 150 distally to force jaws 120, 110 back to the closed position of FIG. 13. Note that outer tube (elongated member) 20 has slots 20b (FIG. 3) to accommodate pins 125, 115.

Shaft 130 has a ball 132 at its distal end 131, preferably integral therewith, and configured and dimensioned to fit within the hemispherical recesses (e.g. recess 119) of jaws 110, 120, respectively. The hemispherical recesses together form a spherical recess. Shaft 130 is supported within a recess in rib 31b in housing half 32a and a corresponding rib in housing half 32b (see FIG. 2).

Turning now to the handle assembly 30 and with initial reference to FIGS. 1 and 2, the assembly 30 includes first and second body halves 32a, 32b fastened together by conventional methods. The handle assembly 30 has a stationary handle or grip 34 with finger loop 28, a movable grasper handle or actuator 40 with finger loop 42, and a cutting handle or actuator 46 with finger loop 48. As shown, grasper handle 40 is positioned proximally of stationary handle 34 and cutter handle 46 is positioned distally of stationary handle 34. Grasping handle 40 is operably associated with the grasper gear 82 and cutter handle 46 is operably associated with cutter gear 86. The body halves have slots to receive the mounting portions of the handles and to accommodate movement of the handles 40, 46.

Referring to FIGS. 2 and 4, yoke 43 of grasper handle 40 has spaced openings 43a for mounting to handle pin 37a of housing 32a and a corresponding handle pin on housing half 32b. Yoke 47 of cutter handle 46 has spaced openings 43a for mounting to handle pin 38a of housing 32a and a corresponding handle pin on housing half 32b.

Grasper handle 40 has an internal cam slot 49 which is configured to receive lower gear pin 85a extending from a lower portion of lower grasper spur gear 85. In this manner, when grasper handle 40 is retracted, i.e. moved in a proximal direction from the position of FIG. 4 to the position of FIG. 7, the cam slot 49 forces lower gear pin 85a proximally to retract grasper gears 85 and 84 proximally. This retracts the attached grasper tube 140 to open the jaws 110, 120 in a grasping fashion described above. This movement can be appreciated by comparing FIGS. 4 and 7—FIG. 4 corresponding to the position of the jaws 110, 120 in the closed position of FIG. 5; and FIG. 7 corresponding to the position of the jaws 110, 120 in the open grasping orientation of FIG. 8. Movement of the grasper handle 40 distally back to its initial at rest position cams the lower gear pin 85a distally to move the grasper gear 84 distally back to its original position, thereby moving the grasper tube 140 distally to pivot the jaws 110, 120 back to the closed position. Note that as shown in FIG. 4, the lower gear pin 85a is below and distal of the pivot axis (extending through openings 43a) of grasper handle 40.

Referring to FIG. 9, cutter handle 46 has an internal cam slot 41 which is configured to receive lower gear pin 89a extending from lower grasper inverted spur gear 89. In this manner, when cutter handle 46 is moved in a distal direction, the lower gear pin 89a is cammed proximally to move the lower cutter spur gear 89 and cutter gear 88 proximally. This retracts the attached cutter tube 150 to open the jaws 110, 120 in a cutting fashion described above. This movement can be appreciated by comparing FIGS. 9 and 12—FIG. 9 corresponding to the position of the jaws 110, 120 in the closed position of FIG. 13; and FIG. 12 corresponding to the position of the jaws 110, 120 in the open cutting orientation of FIG. 11. Movement of the cutter handle 46 proximally back to its initial at rest position cams the lower gear pin 89a distally to move the cutter gear 88 distally back to its original position, thereby moving the cutter tube 150 distally to pivot the jaws 110, 120 back to the closed position. Note in the position of FIG. 7, lower gear pin 89a is above and distal of the pivot axis (extending through openings 47a) of cutter handle 46.

Figure 6:
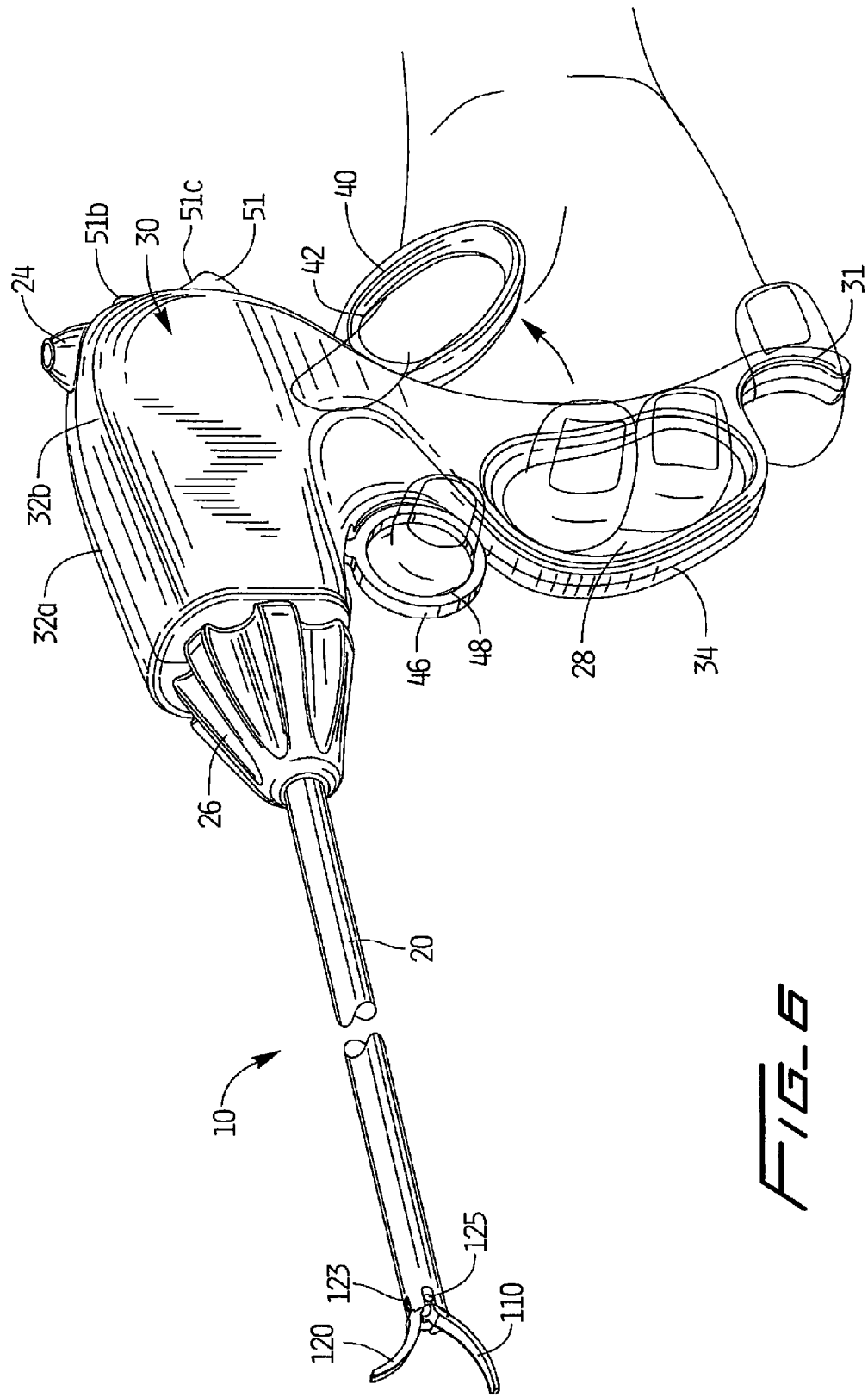
FIG. 6 is a perspective view similar to FIG. 1 showing the grasper handle in the retracted position and the jaws in an open grasping position, the switch remaining in the grasping function position.

The handle assembly provides an ergonomic handle design for moving the jaws as well as a built in safety. This is depicted in FIGS. 1, 6 and 10 which illustrate a surgeon's hand engaging the handle assembly 40. As shown in FIG. 1, both the grasping handle loop 42 and the cutting handle loop 48 of handles 40, 46, respectively, are in the at rest position so that the jaws 110, 120 are closed. The user's thumb is disengaged from grasper loop 42 to access switch 51 on housing 30. The switch 51 is in the grasping function position.

If the user desires to perform a grasping function, the instrument is held as shown with the thumb of the user through grasper loop 42 and the forefinger remaining through the cutter loop 48 (alternatively the forefinger can be removed from the cutter loop 48 during the grasping actuation). The middle and ring finger extend through the handle loop 28 of stationary handle 34. To open the jaws to grasp tissue, the user with his/her thumb moves the grasper handle 40 away from the stationary handle 34 in the direction of the arrow of FIG. 6. This moves the jaws 110, 120 to the open grasping position of FIG. 8. The user then moves the grasper handle 40 distally. i.e. back towards the stationary handle 34 to move the jaws 110, 120 toward each other to grasp tissue therebetween. The jaws 110, 120 move such that the top surface of the bottom jaw 110 and the bottom surface of the top jaw 120 move toward each other in a pivoting fashion.

To switch to the cutting function, the instrument 10 is grasped as shown in FIG. 10 with the thumb of the user removed from the grasper loop 42 to access switch 51. Switch 51 switches the linkage mechanism of the instrument between a grasping and a cutting function such that only one function can be operable at a time as described in detail above. Switch 51 can be activated by the single hand of the user only when the jaws are in the closed position. The ergonomic design of the handle achieves this as: 1) the thumb of the user needs to be removed from the grasper loop 42 to access the switch 51 so that the grasper handle 40 can no longer be held in its outward (open) position to open the jaws; and 2) to reach the switch 51 with the thumb, the grasper handle 40 is blocked in the inward (closed) position by the palm of the user's hand as shown in FIG. 10. A safety mechanism can also be provided to ensure the switch 51 can be activated only when the jaws 110, 120 are closed. This is described below in conjunction with the embodiment of FIG. 15.

After the switch 51 is rotated to the cutting position by pressing the lower portion 51c of the switch 51, it actuates the linkage mechanism as described above to lock the grasper gear 84 and grasper handle 40 to thereby lock movement of the jaws 110, 120 in a grasping function. To effectuate cutting, the forefinger of the user remains in the cutter loop 48 of cutter handle 46 and the thumb remains either outside the grasper loop 42 of grasper handle 40, resting on the rear of housing 32 as shown in FIG. 1 or inside the lop 42 as in FIG. 6. The remaining fingers are also in the same position as in the grasping and switching function, i.e. the middle and ring fingers extending through the handle loop 28 of stationary handle 34. A groove 31 can optionally be provided on stationary handle 34 for resting of the small finger.

To open the jaws in a scissor like fashion to cut/sever tissue, the user with his/her forefinger moves the cutter handle 46 away from the stationary handle 34. This moves the jaws 110, 120 to the open cutting position of FIG. 11. To close the jaws 110, 120, the grasper loop 46 is moved back towards the stationary handle 34. Note, as described above, in the cutting function, the jaws 110, 120 move such that the inner edges of the jaws move toward/across each other in a scissor like fashion. This can be appreciated by comparing FIGS. 11 and 13.

If the user wants to return to the grasping function, the user grasps the handle assembly 30 in the manner shown in FIG. 1 and presses the upper portion 51b of switch 51 to pivot the switch 51 from the position of FIG. 10 to the position of FIG. 1. This actuates the linkage mechanism to lock the cutter gear 88 and cutter handle 46 as described above (and releases the grasper spur gear lock on the grasper gear 84). The user can then grasp the instrument as shown in FIG. 6 to move the jaws 110, 120 in a grasping function. As can be appreciated, the instrument is designed so it can't be switched with the grasping hand of the user between cutting and grasping functions unless the jaws 30 are in the closed position.

In addition or as an alternative to the ergonomic design having this built in safety, a safety mechanism 160 can also be provided. This is shown in the alternative embodiment of FIGS. 15 and 16. The embodiment of FIG. 15 is identical to the embodiment of FIG. 1 except for the safety mechanism and the apertures in the switch. Therefore, the actuator handles, links, etc. have not been labeled for clarity. Corresponding parts with the FIG. 1 embodiment discussed in conjunction with the safety mechanism 160 have been given "prime" designations.

The safety mechanism 160 includes a slidable locking plate 171 having a post 172 extending from a proximal portion 174. Spring 176 biases the locking plate 172 in a distal direction. Inner tab 178 at the proximal portion 174 abuts or engages the rear wall of the grasper gear 84' and inner tab 179 at the distal portion 175 of plate 171 abuts or engages the rear wall of the cutter gear 88'. In the closed position of the jaws 110, 120, both grasper gear 84' and cutter gear 88' are in the forward position. In this position, the locking plate is biased distally by spring 176, out of engagement with switch 180.

If the jaws are in the open cutting position, cutting gear 88' is in the retracted position of FIG. 16, which moves locking plate 171 to a retracted position against the force of spring 176. In this retracted position, the post 172 is positioned in a lower aperture 181a of the switch 180. In this position, the switch 180 cannot be moved as its pivotable movement is blocked. Similarly, if the jaws are in the open grasping position, (with the switch 51 in the grasping function position with the upper portion 51b closer to the housing 32) grasper gear 84' is in the retracted position, which moves locking plate 171 to a retracted position against the force of spring 176. In this retracted position, the post 172 is positioned in an upper aperture 181b of the switch 51 to prevent pivotable movement of the switch 180. Note besides the apertures 181a, 181b, switch 180 is identical to switch 51 described above.

The use of the instrument will now be described. For purposes of this description, the instrument is packaged with the switch 51 in the grasping function position so it's initially ready for grasping; however, the instrument can alternatively be packaged with the switch 51 in the cutting function position. Note that the switch 51 preferably includes indicia on its rear surface so the user has a visual indication of which function the switch 51 is engaged. Also, throughout the description of use, reference is made to how the safety mechanism 160 of FIGS. 15 and 16, if utilized, would function.

In the initial position of the instrument 10 shown in FIG. 1, the grasper handle 40 is in the forward (distal) position, spaced closer to the stationary handle 34 so that jaws 110 and 120 are in the closed position of FIG. 5. The cutter handle 46 is in the retracted (proximal) position, closer to the stationary handle 34. The instrument 10 is inserted through an access port or opening with the jaws 110, 120 closed.

In this initial position, the switch 51 is in the grasping position such that upper portion 51b is angled toward the handle housing 30 and the lower portion 51c is angled away from the housing 32. In this position, shown in FIG. 4, rocker engaging link 56 is angled upwardly (in the orientation of FIG. 4), causing rear intermediate links 60a, 60b, to be angled upwardly. This results in front intermediate link 64 applying a force to curved link 70 so the curved link 70 is pivoted forwardly (counterclockwise) about central housing pin 73 toward cutter gear 88 to move teeth 86a of cutter spur gear 86 into engagement with the teeth 88a of cutter gear 88. Consequently, this intermeshing of the teeth 86a and teeth 88a locks gear 88 so movement is prohibited. Thus, the user cannot move cutter handle 46 and cannot advance cutter actuator 150. With the locking of cutter handle 46, the user is prevented from confusing the cutting and grasping function. Note that the teeth 82a of the grasper spur gear 82 in this position are spaced (disengaged) from the teeth 84a of the grasper gear 84 to allow movement of gear 84.

Note also in the closed position of the jaws 110, 120, the cutter gear 88 and grasper gear 84 (and lower spur gears 85, 89) are in the forward position so that in the embodiment of FIGS. 15 and 16 utilizing safety mechanism 160, safety plate 171 is in the forward position. In this forward (disengaged) position, the proximal post 172 of safety plate 171 is disengaged from the switch 180 and is spaced distally from the apertures 181a, 181b to enable pivoting movement of switch 180.

The instrument 10 is inserted with the jaws 110, 120 closed through an access port or opening and advanced toward the surgical site. If the surgeon desires to use the grasping function, the user retracts grasper handle 40 in the direction of the arrow of FIGS. 6 and 7, moving it away from the stationary handle 34. When the grasper handle 40 is moved in this direction, handle 40 pivots about handle mounting pin 37a (FIG. 2) and forces gear 84 proximally via engagement of grasper lower gear pin 85a of attached lower spur gear 89 in cam slot 49 (FIG. 7). This causes retraction of grasper tube 140 to retract attached yoke 136 which pivots the jaws 110, 120 about pivot axis D (FIG. 5) in the grasping orientation from the closed position to the grasping open position of FIG. 8 via the engagement of upper and lower jaw pins 123, 113.

Note that in this retracted position of the grasper gear 84, if the safety mechanism 160 of FIG. 15 is utilized, safety plate 171 is likewise retracted (due to its abutment with the back of the grasper gear 84). In this retracted position, post 172 is positioned within aperture 181b of switch 180. This prevents movement of switch 51 so the user cannot switch from the grasping function to the cutting function if the jaws 110, 120 are in the open position.

To close the jaws in this grasper function to grasp tissue positioned between the jaws 110, 120, grasper handle 40 is moved in the opposite direction (distally toward stationary handle 34) thereby moving grasper gear 84 via lower gear pin 85 distally to advance grasper tube 140 so jaws 110, 120 can pivot about pivot axis D back to the closed position of FIG. 5.

If the surgeon desires to switch to the cutting function of the instrument 10, the user pivots switch 51 to its cutting function position by pressing lower portion 51c toward housing 32 so that the lower portion 51c is closer to handle housing 32 and the upper portion 51b is positioned further away from housing 32 as shown in FIG. 10. Note that detents 51a of switch 51 are moved from engagement with upper slot 33b in housing half 32a (FIG. 2) into engagement with lower slot 33a of housing half 32a (and a corresponding slot in housing half 32b) to provide a tactile indicator that the switch 51 is in the cutting position as well as to maintain the switch 51 in this position so the user does not need to hold the switch 51.

Such pivoting motion of switch 51 pulls attached link 56 proximally, which in turn pulls rear intermediate link 60a 60b proximally to the more linear position of FIG. 9. This forces front intermediate link 64 to pivot curved link 70 in a clockwise direction about central mounting pin 73. This clockwise movement lifts cutter spur gear 86 out of locking engagement with cutter gear 88 and moves grasper spur gear 82 into locking engagement with grasper gear 84. In this grasper locking position, teeth 82a of spur gear 82 intermesh with teeth 84*a* of grasper gear 84 so that movement of the grasper gear 84 is prohibited. Thus, the user cannot move grasper handle 40 to actuate grasper tube 140.

Note again that if the safety mechanism 160 of FIGS. 15 and 16 is used, in the closed position of the jaws 110, 120, the safety plate 171 is in the forward position as both the cutter gear 88 and grasper gear 84 are in the forward position. In this forward (disengaged) position, the proximal post 172 of safety plate 171 is disengaged from the apertures 181*a*, 181*b* of switch 180 as it is spaced distally from the apertures.

To move jaws 110, 120 in a cutting function, the user moves cutter handle 46 distally, moving it in a direction away toward stationary handle 34 as shown in FIG. 12. When the cutter handle 46 is moved in this direction, cutter handle 46 pivots about handle mounting pin 38*a* (FIG. 2) and cutter lower gear pin 89*a* of lower inverted spur gear 89 (attached to cutter gear 88) is cammed rearwardly by internal cam slot 47 of cutter handle 40. This causes retraction of cutter gear 88 which retracts attached cutter tube 150. Retraction of cutter tube 150 pivots the jaws 110, 120 about pivot axis A in the cutting orientation to an open cutting position as side pins 115 and 125 are engaged by extensions 153*a*,153*b* of cutter tube 150 (see FIG. 11).

Note that in this retracted position of the cutter gear 86, safety plate 171, if provided, is likewise retracted (due to its abutment with the back of the cutter gear 86). In this retracted position, post 172 is positioned within aperture 181*a* of switch 180. This prevents movement of switch 180 so the user cannot switch from the cutting function to the grasping function if the jaws 110, 120 are in the open position.

To close the jaws 110, 120, the cutter handle 46 is moved proximally toward the stationary handle 34 back to its at rest position, thereby advancing the cutter gear 86 and cutter tube 150 distally.

As can be appreciated, if the user desires to switch from the cutting function to the grasping function, switch 51 is pivoted so upper portion 51*c* is pressed toward the housing 32. As noted above, the jaws 110, 120 need to be in the closed position to activate the switch 51 because of safety plate 171. Detents 51*a* are moved from upper recess 33*b* to upper recess 33*a* of housing 32, again providing a tactile indicator that the switch 51 is in position. Such pivoting motion of the switch 51 forces links 56 and 60*a*, 60*b*, to the angled position of FIG. 4, causing intermediate link 64 to rotate curved link 70 in a counterclockwise direction to lift grasper spur gear 82 out of engagement with grasper gear 84 and to move cutter spur gear 86 into locking engagement with cutter gear 88. Thus, as described above, cutter handle 46 is locked and cannot be moved and the jaws 110, 120 can be opened in a grasping function. Safety plate 171 is out of locking engagement with switch 51.

As can be appreciated, the user can activate the switch to choose between the cutting and grasping functions as often as desirable. Thus, for example, in a laparoscopic cholecystectomy procedure, the surgeon can use instrument 10 to dissect tissue with the open jaws 110, 120, sever the duct with the jaws 110, 120 and then grasp the gall bladder with jaws 110, 120, avoiding the need for multiple instruments and instrument exchanges.

It should be appreciated that the instrument can alternatively be provided with different jaws to perform other functions beside grasping and cutting. The switching mechanism would enable switching between the two different functions.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical instrument for performing first and second different functions on tissue comprising:
   an elongated member;
   a first jaw positioned adjacent a distal portion of the elongated member;
   a second jaw positioned adjacent the distal portion of the elongated member and mounted for movement with respect to the first jaw, the first and second jaws relatively movable between open and closed positions in a first orientation and further movable between open and closed positions in a second different orientation;
   a first actuating mechanism for moving the jaws in the first orientation;
   a first handle for moving the first actuating mechanism;
   a second actuating mechanism for moving the jaws in the second orientation;
   a second handle for moving the second actuating mechanism; and
   a switch for choosing the first or second actuating mechanism, wherein the switch can be activated only when the jaws are in the closed position, and the switch preventing movement of one of the first and second handles while enabling movement of the other of the first and second handles.

2. The instrument of claim 1, wherein the first jaw has a first upper surface with a first edge and a second edge and the second jaw has a second lower surface with a third edge and a fourth edge, wherein when the jaws move between open and closed positions in the first orientation to perform a cutting function, the first and third edges pass each other in substantially parallel planes and when the jaws move between open and closed positions in the second orientation in a grasping function, the first and third edges pivot away from each other in transverse planes.

3. The instrument of claim 1, wherein movement of the switch moves a link in a clockwise or counterclockwise direction to effect operative engagement of one of the actuating mechanisms to prevent movement thereof.

4. The instrument of claim 1, further comprising a safety member operably associated with the switch, the safety member movable between a first position to lock the switch against movement and a second position to allow movement of the switch, the safety automatically locking the switch when the jaws are in the open position.

5. The instrument of claim 4, wherein the safety member engages an aperture in the switch.

* * * * *